(12) United States Patent
Svendsen et al.

(10) Patent No.: US 8,017,351 B2
(45) Date of Patent: Sep. 13, 2011

(54) AMYLASES FOR PHARMACEUTICAL USE

(75) Inventors: Allan Svendsen, Horsholm (DK); Peter Collin Gregory, Hannover (DE)

(73) Assignees: Novozymes A/S, Bagsvaerd (DK); Solvay Pharmaceuticals GmbH, Hannover (DE)

( * ) Notice: Subject to any disclaimer, the term of this patent is extended or adjusted under 35 U.S.C. 154(b) by 542 days.

(21) Appl. No.: 11/917,551

(22) PCT Filed: Jun. 16, 2006

(86) PCT No.: PCT/DK2006/000354
§ 371 (c)(1),
(2), (4) Date: Dec. 14, 2007

(87) PCT Pub. No.: WO2006/136161
PCT Pub. Date: Dec. 28, 2006

(65) Prior Publication Data
US 2009/0035293 A1 Feb. 5, 2009

(30) Foreign Application Priority Data
Jun. 24, 2005 (DK) .................. 2005 00931

(51) Int. Cl.
*C12Q 1/40* (2006.01)
*C12N 9/28* (2006.01)
(52) U.S. Cl. ............... 435/22; 435/202; 536/23.2
(58) Field of Classification Search ........... 435/22, 435/202; 536/23.2
See application file for complete search history.

(56) References Cited

U.S. PATENT DOCUMENTS

| | | | |
|---|---|---|---|
| 6,410,295 B1 * | 6/2002 | Andersen et al. | 435/202 |
| 7,306,936 B2 * | 12/2007 | Andersen et al. | 435/203 |
| 7,625,737 B2 * | 12/2009 | Svendsen et al. | 435/202 |

FOREIGN PATENT DOCUMENTS

| | | |
|---|---|---|
| EP | 0 594 235 | 4/1994 |
| EP | 0 600 868 | 4/1999 |
| EP | 0 828 509 | 1/2005 |
| RU | 2201763 | 10/2003 |
| WO | WO 96/38170 A1 | 12/1996 |
| WO | WO 99/19467 | 4/1999 |
| WO | WO 00/54799 | 9/2000 |
| WO | WO 01/62280 | 8/2001 |
| WO | WO 02/060474 | 8/2002 |
| WO | WO 2004/078960 | 9/2004 |

OTHER PUBLICATIONS

Svendsen et al., Database Geneseq, Database Accession No. AAW31406 (XP-002419749) (1998).
Gray et al., Journal of Bacteriology, vol. 166, No. 2, pp. 635-643 (1986).
Boel 1998, GenBank Database Accession No. AAC08588—lipase [Thermomyces lanuginosus].
Gray et al. 1993, GenBank Database Accession No. AAA22240—amyS [*Bacillus licheniformis*].
Jorgensen et al. 1996, GenBank Database Accession No. 1713273A—Alpha Amylase.
Ramnani et al. 2004, GenBank Database Accession No. AAS86761—keratinase [*Bacillus licheniforrnis*].
Tsukamoto et al. 1993, GenBank Database Accession No. AAA22231—G6-amylase precursor [*Bacillus* sp.].

* cited by examiner

*Primary Examiner* — Tekchand Saidha
(74) *Attorney, Agent, or Firm* — Michael W. Krenicky

(57) ABSTRACT

The pharmaceutical use of amylases related to *Bacillus* alpha-amylases of SEQ ID NOs: 1-3, optionally in combination with a lipase and/or a protease. Examples of medical indications are: Treatment of digestive disorders, pancreatic exocrine insufficiency (PEI), pancreatitis, cystic fibrosis, diabetes type I, and/or diabetes type II. The amylases of SEQ ID NOs: 1-3 are variants of amylases from *Bacillus stearothermophilus*, *Bacillus licheniformis* and *Bacillus* sp. The amylases of the invention have an improved efficacy in vivo, an improved pH-profile, a high specific activity, and/or an improved starch degradation profile.

20 Claims, 2 Drawing Sheets

US 8,017,351 B2

AMYLASES FOR PHARMACEUTICAL USE

CROSS-REFERENCE TO RELATED APPLICATIONS

This application is a 35 U.S.C. 371 national application of PCT/DK2006/000354 filed Jun. 16, 2006, which claims priority or the benefit under 35 U.S.C. 119 of Danish application no. PA 2005 00931 filed Jun. 16, 2006 and of U.S. provisional application no. 60/694,169 filed Jun. 27, 2005, the contents of which are fully incorporated herein by reference.

TECHNICAL FIELD

The present invention relates to the pharmaceutical use of amylases related to certain *Bacillus* alpha-amylases (SEQ ID NOs: 1-3), optionally in combination with a lipase and/or a protease. Examples of medical indications are: Treatment of digestive disorders, pancreatic exocrine insufficiency (PEI), pancreatitis, cystic fibrosis, diabetes type I, and/or diabetes type II.

BACKGROUND ART

Several commercial medicaments in the form of pancreatic enzyme supplements are known for the treatment of pancreatic exocrine insufficiency. The active ingredients of these products are digestive enzymes, mainly amylase, lipase and protease, which are normally produced in the pancreas and excreted to the upper part of the small intestine (the duodenum). The enzymes used in such medicaments derive from bovine or swine pancreas, however there are also products on the market with microbial enzymes, e.g. the product Nortase® which contains a lipase from *Rhizopus oryzae*, a protease from *Aspergillus oryzae*, and an amylase from *Aspergillus oryzae*.

U.S. Pat. No. 5,614,189 (EP 600868) describes the use of, i.a., a lipase derived from *Humicola lanuginosa* in pancreatic enzyme replacement therapy, for example in the treatment of patients suffering from cystic fibrosis. This lipase is from *Humicola lanuginosa* DSM 4109 and has the amino acid sequence of amino acids 1-269 of SEQ ID NO: 9 herein.

WO 00/54799 describes the use of physiologically acceptable enzyme mixtures having lipolytic, proteolytic and amylolytic activity in the treatment of diabetes mellitus type I and II.

WO 02/060474 describes the use of a concentrated lipase from *Rhizopus delemar*, a neutral protease from *Aspergillus melleus*, and an amylase from *Aspergillus oryzae* in the treatment of maldigestion.

WO 01/62280 describes the use of a non-fungal lipase crystal crosslinked with a multifunctional crosslinking agent, a protease, and an amylase, wherein the lipase crystal is active at a pH range from about 2.0 to 9.0, for treating or preventing a gastrointestinal disorder in a mammal. A preferred lipase is from *Pseudomonas*, preferred amylases are from *Aspergillus* and *Bacillus*, preferred proteases are bromelain, papain or ficin.

EP 0828509 describes the use of certain acid-stable amylases, optionally in combination with certain acid-stable lipases and/or proteases, in the treatment of exocrine pancreas insufficiency. A preferred amylase is from *Aspergillus niger*, and preferred lipases are from *Rhizopus arrhizus* or *Rhizopus javanicus*.

WO 99/19467 describes certain variants of alpha-amylases derived from *Bacillus stearothermophilus*, *Bacillus licheniformis*, and *Bacillus amyloliquefaciens*, as well as various industrial uses thereof, however not the pharmaceutical use. The sequences of these wildtype *Bacillus* alpha-amylases designated SEQ ID NOs: 3-5 in WO 99/19467 are included herein as SEQ ID NOs: 10-12, respectively.

EP 0594235 describes a method for preparing purified amylase from a fermentation broth. A pharmaceutical composition is also claimed, and a potential use as digestive aid is mentioned, along with other potential uses. The examples illustrate the claimed purification method for a *Bacillus licheniformis* alpha-amylase.

WO 2004/078960 discloses a method for identifying at least one T-cell epitope of an amylase and variant amylases comprising at least one alteration in at least one epitope. Many potential uses are enumerated, including the pharmaceutical use. An amylase from *Bacillus licheniformis* is referred to.

EP 0828509 describes the use of certain acid-stable amylases, optionally in combination with certain acid-stable lipases and/or proteases, in the treatment of exocrine pancreas insufficiency. A preferred amylase is from *Aspergillus niger*, and preferred lipases are from *Rhizopus arrhizus* or *Rhizopus javanicus*.

There is a need in the art for alternative, preferably improved, enzymes for pharmaceutical use.

SUMMARY OF THE INVENTION

The present invention provides alternative, preferably improved, enzymes for pharmaceutical use, in particular for the treatment of digestive disorders, pancreatic exocrine insufficiency (PEI), pancreatitis, cystic fibrosis, diabetes type I, and/or diabetes type II. The new enzymes are proteases, amylases, and lipases. Preferably, the enzymes for use according to the invention have an improved efficacy in vivo and/or in vitro; an improved pH-activity profile; an improved specific activity; an improved degradation profile; are active in the presence of bile salts; and/or have a reduced allergenicity.

The present invention relates to an amylase of at least 50% identity to (i) amino acids 1-481 of SEQ ID NO: 1, (ii) amino acids 1-481 of SEQ ID NO: 2, and/or (iii) amino acids 1-483 of SEQ ID NO: 3; for use as a medicament, optionally in combination with a lipase, and/or a protease.

The invention also relates to the use of such amylases for the manufacture of a medicament for the treatment of digestive disorders, PEI, pancreatitis, cystic fibrosis, diabetes type I, and/or diabetes type II, these uses optionally further comprising the use of a lipase, and/or a protease.

The invention furthermore relates to a pharmaceutical composition comprising such amylases, together with at least one pharmaceutically acceptable auxiliary material, optionally including a lipase and/or a protease.

The invention also relates to a method for the treatment of digestive disorders, PEI, pancreatitis (acute and/or chronic), cystic fibrosis, diabetes type I, and/or diabetes type II, by administering a therapeutically effective amount of such amylases, optionally together with a lipase and/or a protease.

DETAILED DESCRIPTION OF THE INVENTION

Enzymes

Figure 1:
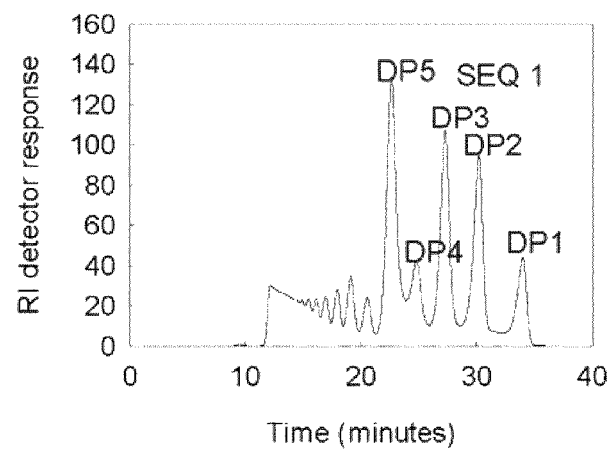
FIG. 1 shows a chromatogram representing the degradation profile of an amylase having the amino acid sequence of amino acids 1-486 of SEQ ID NO: 1 (a *Bacillus stearothermophilus* amylase variant)

The present invention relates to the pharmaceutical use of amylases having at least 50% identity to (i) amino acids 1-481 of SEQ ID NO: 1, (ii) amino acids 1-481 of SEQ ID NO: 2, and/or (iii) amino acids 1-483 of SEQ ID NO: 3; for use as a medicament. The invention also relates to the use of such amylases for the manufacture of a medicament for the treatment of digestive disorders, PEI, pancreatitis (acute and/or chronic), cystic fibrosis, diabetes type I, and/or diabetes type II. The invention furthermore relates to a pharmaceutical composition comprising such amylases, together with at least one pharmaceutically acceptable auxiliary material. The invention furthermore relates to a method for the treatment of the diseases mentioned above by administering a therapeutically effective amount of such amylases.

In what follows, the amylase for use in the compositions, methods and uses of the invention is referred to as the "amylase of the invention."

In the present context, an amylase is an enzyme that catalyzes the endo-hydrolysis of starch and other linear and branched oligo- and polysaccharides. In a particular embodiment, the amylase for use according to the invention has alpha-amylase activity, viz. catalyzes the endohydrolysis of 1,4-alpha-glucosidic linkages in oligosaccharides and polysaccharides. Alpha-amylases act, e.g., on starch, glycogen and related polysaccharides and oligosaccharides in a random manner, liberating reducing groups in the alpha-configuration.

In a preferred embodiment the amylase of the invention is an alpha-amylase (systematical name: 1,4-alpha-D-glucan glucanohydrolase). In further embodiments, the amylase of the invention belongs to the EC 3.2.1.-group of amylases, such as EC 3.2.1.1 (alpha-amylase), EC 3.2.1.2 (beta-amylase), EC 3.2.1.3 (glucan 1,4-alpha-glucosidase, amyloglucosidase, or glucoamylase), EC 3.2.1.20 (alpha-glucosidase), EC 3.2.1.60 (glucan 1,4-alpha-maltotetraohydrolase), EC 3.2.1.68 (isoamylase), EC 3.2.1.98 (glucan 1,4-alpha-maltohexosidase), or EC 3.2.1.133 (glucan 1,4-alpha-maltohydrolase). In a preferred embodiment, the amylase for use according to the invention can be, or is, classified as belonging to the EC 3.2.1.1 group. The EC numbers refer to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web at http://www.chem.qmw.ac.uk/iubmb/enzyme/index.html.

In particular embodiments, the amylase of the invention has a degree of identity to any one of (i) amino acids 1-481 of SEQ ID NO: 1, (ii) amino acids 1-481 of SEQ ID NO: 2, and/or (iii) amino acids 1-483 of SEQ ID NO: 3 of at least 51%, 52%, 53%, 54%, 55%, 56%, 57%, 58%, 59%, or at least 60%. In other particular embodiments, the amylase of the invention has a degree of identity to any one of (i) amino acids 1-481 of SEQ ID NO: 1, (ii) amino acids 1-481 of SEQ ID NO: 2, and/or (iii) amino acids 1-483 of SEQ ID NO: 3 of at least 61%, 62%, 63%, 64%, 65%, 66%, 67%, 68%, 69%, or at least 70%. In additional particular embodiments, the amylase of the invention has a degree of identity to any one of (i) amino acids 1-481 of SEQ ID NO: 1, (ii) amino acids 1-481 of SEQ ID NO: 2, and/or (iii) amino acids 1-483 of SEQ ID NO: 3 of at least 71%, 72%, 73%, 74%, 75%, 76%, 77%, 78%, 79%, or at least 80%. In other particular embodiments, the amylase of the invention has a degree of identity to any one of (i) amino acids 1-481 of SEQ ID NO: 1, (ii) amino acids 1-481 of SEQ ID NO: 2, and/or (iii) amino acids 1-483 of SEQ ID NO: 3 of at least 81%, 82%, 83%, 84%, 85%, 86%, 87%, 88%, 89%, or at least 90%. In still further particular embodiments, the amylase of the invention has a degree of identity to any one of (i) amino acids 1-481 of SEQ ID NO: 1, (ii) amino acids 1-481 of SEQ ID NO: 2, and/or (iii) amino acids 1-483 of SEQ ID NO: 3 of at least 91%, 92%, 93%, 94%, 95%, 96%, 97%, 98%, or at least 99%.

In a further particular embodiment, the amylase of the invention comprises at least one substitution, deletion, and/or insertion of one or more amino acids in any one of the sequences of (i) amino acids 1-481 of SEQ ID NO: 1, (ii) amino acids 1-481 of SEQ ID NO: 2, and/or (iii) amino acids 1-483 of SEQ ID NO: 3. Preferably, the amino acid changes are of a minor nature, that is conservative amino acid substitutions or insertions that do not significantly affect the folding and/or activity of the protein; small deletions; small amino- or carboxyl-terminal extensions, such as an amino-terminal methionine residue; a small linker peptide; or a small extension that facilitates purification by changing net charge or another function, such as a poly-histidine tract, an antigenic epitope or a binding domain. In the above context, the term "small" independently designates a number of up to 25 amino acid residues. In preferred embodiments, the term "small" designates up to 24, 23, 22, 21, or up to 20 amino acid residues. In additional preferred embodiments, the term "small" independently designates up to 19, 18, 17, 16, 15, 14, 13, 12, 11, or up to 10 amino acid residues. In further preferred embodiments, the term "small" independently designates up to 9, 8, 7, 6, 5, 4, 3, 2, or up to 1 amino acid residue. In alternative embodiments, the term "small" independently designates up to 40, 39, 38, 37, 36, 35, 34, 33, 32, 31, 30, 29, 28, 27, 26, or up to 25 amino acid residues.

Examples of conservative substitutions are within the group of basic amino acids (arginine, lysine and histidine), acidic amino acids (glutamic acid and aspartic acid), polar amino acids (serine, threonine, glutamine and asparagine), hydrophobic amino acids (leucine, isoleucine, valine and alanine), aromatic amino acids (phenylalanine, tryptophan and tyrosine), and small amino acids (glycine, alanine, proline, serine, threonine, cysteine and methionine).

In the alternative, examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In additional embodiments, the amylase of the invention has an amino acid sequence which differs by no more than 25, 24, 23, 22, 21, 20, 19, 18, 17, 16, 15, 14, 13, 12, or no more than 11 amino acids from any one of (i) amino acids 1-481 of SEQ ID NO: 1, (ii) amino acids 1-481 of SEQ ID NO: 2, and/or (iii) amino acids 1-483 of SEQ ID NO: 3; or, it differs from any one of (i) amino acids 1-481 of SEQ ID NO: 1, (ii) amino acids 1-481 of SEQ ID NO: 2, and/or (iii) amino acids 1-483 of SEQ ID NO: 3 by no more than 10, 9, 8, 7, 6, 5, 4, 3, 2, or by no more than 1 amino acid. In alternative embodiments, the amylase of the invention has an amino acid sequence which differs by no more than 40, 39, 38, 37, 36, 35, 34, 33, 32, 31, 30, 29, 28, 27, or no more than 26 amino acids from any one of (i) amino acids 1-481 of SEQ ID NO: 1, (ii) amino acids 1-481 of SEQ ID NO: 2, and/or (iii) amino acids 1-483 of SEQ ID NO: 3.

In still further particular embodiments, the amylase of the invention is an allelic variant of any one of the amylases having (i) amino acids 1-481 of SEQ ID NO: 1, (ii) amino acids 1-481 of SEQ ID NO: 2, and/or (iii) amino acids 1-483 of SEQ ID NO: 3, or a fragment thereof that has amylase activity. The amylase of the invention may also be an allelic variant of any one of the amylases having the amino acid sequences of SEQ ID NO: 10, SEQ ID NO: 11, and SEQ ID NO: 12. The term allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. The term fragment is defined herein as a polypeptide having one or more amino acids deleted from the amino and/or carboxyl terminus of SEQ ID NO: 1, SEQ ID NO: 2 or SEQ ID NO: 3, preferably having one or more amino acids deleted from the amino and/or carboxyl terminus of amino acids 1-481, 1-484, 1-486, or 1-513 of SEQ ID NO: 1; of amino acids 1-481 of SEQ ID NO: 2, or of amino acids 1-483 of SEQ ID NO: 3. Preferably, a small number of amino acids has been deleted, small being defined as explained above. More preferably, a fragment contains at least 440, 441, 442, 443, 444, 445, 446, 447, 448, 449, 450, 451, 452, 453, or at least 454 amino acid residues. Most preferably, a fragment contains at least 452, 453, 454, 455, 456, 457, 458, 459, 460, 461, 462, 463, 464, 465, 466, 467, 468, 469, or at least 470 amino acid residues. Even more preferably, a fragment contains at least 471, 472, 473, 474, 475, 476, 477, 478, 479, or at least 480 amino acid residues.

In summary, one embodiment of the present invention relates to an amylase for pharmaceutical use, wherein a) the amylase comprises an amino acid sequence selected from the group consisting of (i) amino acids 1-481 of SEQ ID NO: 1, (ii) amino acids 1-481 of SEQ ID NO: 2, and/or (iii) amino acids 1-483 of SEQ ID NO: 3; and/or b) the amylase is a variant of an amino acid sequence selected from the group consisting of (i) amino acids 1-481 of SEQ ID NO: 1, (ii) amino acids 1-481 of SEQ ID NO: 2, and/or (iii) amino acids 1-483 of SEQ ID NO: 3, wherein the variant differs from the respective amino acid sequence by no more than twenty-five amino acids, and wherein: (i) the variant comprises at least one substitution, deletion and/or insertion of one or more amino acids as compared to the respective amino acid sequence; and/or (ii) the variant comprises at least one small deletion as compared to the respective amino acid sequence; and/or (iii) the variant comprises at least one small N- or C-terminal extension as compared to the respective amino acid sequence; and/or c) the amylase is an allelic variant of an amylase having amino acids selected from the group consisting of (i) amino acids 1-481 of SEQ ID NO: 1, (ii) amino acids 1-481 of SEQ ID NO: 2, and/or (iii) amino acids 1-483 of SEQ ID NO: 3; and/or d) the amylase is a fragment of an amylase having amino acids selected from the group consisting of (i) amino acids 1-481 of SEQ ID NO: 1, (ii) amino acids 1-481 of SEQ ID NO: 2, and/or (iii) amino acids 1-483 of SEQ ID NO: 3.

In particular, the present invention relates to an amylase for pharmaceutical use, wherein the amylase has an amino acid sequence selected from the group consisting of (i) amino acids 1-481, 1-484, 1-486, or 1-513 of SEQ ID NO: 1, (ii) amino acids 1-481 of SEQ ID NO: 2, and/or (iii) amino acids 1-483 of SEQ ID NO: 3.

In still further particular embodiments of the invention, the amylase is derived from a microorganism, for example from a fungus, or from a bacterium. Examples of bacteria are strains of *Bacillus*, such as strains of *Bacillus amyloliquefaciens, Bacillus circulans, Bacillus halmapalus, Bacillus licheniformis, Bacillus megaterium, Bacillus* sp., *Bacillus stearothermophilus,* and *Bacillus subtilis*; preferably from strains of *Bacillus amyloliquefaciens, Bacillus circulans, Bacillus halmapalus, Bacillus licheniformis, Bacillus megaterium, Bacillus* sp., and *Bacillus stearothermophilus*; most preferably from strains of *Bacillus stearothermophilus, Bacillus licheniformis,* or *Bacillus* sp. In this context, the term "derived from" includes enzymes obtainable, or obtained, from wildtype strains; as well as, preferably, variants thereof having at least one substitution, insertion, and/or deletion of at least one amino acid residue. The term variant also includes shufflants, hybrids, chimeric enzymes and consensus enzymes. The variants may have been produced by any method known in the art, such as site-directed mutagenesis, random mutagenesis, consensus derivation processes (EP 897985), and gene shuffling (WO 95/22625, WO 96/00343), etc.

Non-limiting examples of wildtype amylases of the invention are those derived from *Bacillus licheniformis*, such as Swissprot entry name AMY_BACLI, primary accession number P06278; *Bacillus amyloliquefaciens*, such as Swissprot entry name AMY_BACAM, primary accession number P00692; *Bacillus megaterium*, such as Swissprot entry name AMY_BACME, primary accession number P20845; *Bacillus circulans*, such as Swissprot entry name AMY_BACCI, primary accession number P08137; *Bacillus stearothermophilus*, such as Swissprot entry name AMY_BACST, primary accession number P06279. Another example is from *Bacillus subtilis*, such as Swissprot entry name AMY_BACSU, primary accession number P00691. A still further example is the amylase derived from *Bacillus halmapalus*, amino acids 1-485 of SEQ ID NO: 4. Non-limiting examples of amylase variants for use according to the invention are disclosed in WO 96/23873, WO 99/19467, U.S. Pat. No. 4,933,279, EP 722490, and EP 904360. In particular embodiments, the amylase of the invention (i) is not Swissprot entry name AMY_BACLI, primary accession number P06278; and/or (ii) is not Swissprot entry name AMY_BACST, primary accession number P06279.

Further particular examples of amylases of the invention are the amylases contained in the following commercial products: Clarase, DexLo, GC 262 SP, G-Zyme G990, G-Zyme G995, G-Zyme G997, G-Zyme G998, HTAA, Optimax 7525, Purastar OxAm, Purastar ST, Spezyme AA, Spezyme Alpha, Spezyme BBA, Spezyme Delta AA, Spezyme DBA, Spezyme Ethyl, Spezyme Fred (GC521), Spezyme HPA, and Ultraphlow (all from Genencor); Validase BAA, Validase FAA, Validase HT340L, Valley Thin 340L (all from Valley Research); Avizyme 1500, Dextro 300L, Kleistase, Maltazyme, Maxamyl, Thermozyme, Thermatex, Starzyme HT 120 L, Starzyme Super Conc, and Ultraphlo.

Particularly preferred examples of amylases of the invention are the following: An amylase comprising amino acids 1-481 of SEQ ID NO: 1, such as amylases having amino acids 1-481 of SEQ ID NO: 1, amino acids 1-484 of SEQ ID NO: 1, amino acids 1-486 of SEQ ID NO: 1, or amino acids 1-513 of SEQ ID NO: 1; an amylase having amino acids 1-481 of SEQ ID NO: 2; and an amylase having amino acids 1-483 of SEQ ID NO: 3.

In still further particular embodiments, an additional amylase may be used. Examples of additional amylases are mammalian amylases, and microbial proteases. A preferred mammalian amylase is pancreas extract, e.g. from swine or ox, such as pancreatin. The pancreatin may be used in the form of an uncoated (raw) product, or in the form of a formulated product (enteric coated (to provide resistance against gastric acid), or non-functionally coated (coated, but not to provide resistance against gastric acid)). Pancreatin potentially comprises still further enzymatic active constituents like pancreatic lipase, BSSL (Bile Salt Stimulated Lipase), and/or pancreatic protease. The microbial amylase may, for example, derive from bacterial or fungal strains, such as *Bacillus, Pseudomonas, Aspergillus*, or *Rhizopus*. The amylase may in particular be derived from a strain of *Aspergillus*, such as *Aspergillus niger, Aspergillus oryzae* or *Aspergillus melleus*, for example either of the products Amylase A1™ derived from Aspergillus oryzae which is commercially available from Amano Pharmaceuticals, Japan, or Amylase EC™ derived from *Aspergillus melleus* which is commercially available from Extract-Chemie, Germany.

The amylase of the invention may be used, with or without a lipase as described below, in combination with a protease. The term "protease" is defined herein as an enzyme that hydrolyses peptide bonds. It includes any enzyme belonging to the EC 3.4 enzyme group (including each of the thirteen subclasses thereof, these enzymes being in the following referred to as "belonging to the EC 3.4.-.-group").

The protease may be a mammalian proteases, or a microbial proteases. A preferred mammalian protease is pancreas extract, e.g. from swine or ox, such as pancreatin. The pancreatin may be used in the form of an uncoated (raw) product, or in the form of a formulated product (enteric coated, or non-functionally coated). Pancreatin potentially comprises still further enzymatic active constituents like pancreatic lipase, BSSL, and/or pancreatic amylase. The microbial protease may, e.g., based on or derived from bacterial or fungal strains. The protease may in particular be derived from a strain of *Aspergillus*, such as *Aspergillus oryzae* or *Aspergillus melleus*, in particular the product Prozyme 6™ (neutral, alkaline protease EC 3.4.21.63) which is commercially available from Amano Pharmaceuticals, Japan. Examples of bacterial proteases are proteases from *Bacillus* and *Nocardiopsis*, such as the *Bacillus licheniformis* protease having the amino acid sequence of amino acids 1-274 of SEQ ID NO: 5, the *Nocardiopsis* sp. protease having the amino acid sequence of amino acids 1-188 of SEQ ID NO: 6, or the *Nocardiopsis dassonviellei* subsp. *dassonvillei* protease having the amino acid sequence of amino acids 1-188 of SEQ ID NO: 7. The protease of amino acids 1-274 of SEQ ID NO: 5 may, e.g., be prepared as described in DK patent application no. 2005 00930 entitled "Proteases for Pharmaceutical Use" and filed on Jun. 24, 2005 by Solvay Pharmaceuticals GmbH and Novozymes A/S. The proteases of amino acids 1-188 of SEQ ID NO: 6-7 may, e.g., be prepared as described in WO 2001/58276, or in WO 2004/111224.

In a preferred embodiment, the protease is at least 70% identical to either of (i) amino acids 1-274 of SEQ ID NO: 5, (ii) amino acids 1-188 of SEQ ID NO: 6, and/or (iii) amino acids 1-188 of SEQ ID NO: 7. In additional preferred embodiments of either of (i), (ii) or (iii), the degrees of identity is at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In alternative embodiments of either of (i), (ii), or (iii), the degrees of identity is at least about 50%, 51%, 52%, 53%, 54%, 55%, 56%, 57%, 58%, 59%, 60%, 61%, 62%, 63%, 64%, 65%, 66%, 67%, 68%, or at least 69%.

The amylase of the invention may be used, with or without a protease as mentioned above, in combination with a lipase. In the present context, a lipase means a carboxylic ester hydrolase EC 3.1.1.-, which includes activities such as EC 3.1.1.3 triacylglycerol lipase, EC 3.1.1.4 phospholipase A1, EC 3.1.1.5 lysophospholipase, EC 3.1.1.26 galactolipase, EC 3.1.1.32 phospholipase A1, EC 3.1.1.73 feruloyl esterase. In a particular embodiment, the lipase is an EC 3.1.1.3 triacylglycerol lipase.

The lipase may be a mammalian lipase, or a microbial lipase. A preferred mammalian lipase is pancreas extract, e.g. from swine or ox, such as pancreatin. The pancreatin may be used in the form of an uncoated (raw) product, or in the form of a formulated product (enteric coated, or non-functionally coated). Pancreatin potentially comprises still further enzymatic active constituents like pancreatic protease, BSSL, and/or pancreatic amylase. The microbial lipase may, for example, be derived from bacterial or fungal strains, such as *Bacillus, Pseudomonas, Aspergillus*, or *Rhizopus*. The lipase may in particular be derived from a strain of *Rhizopus*, such as *Rhizopus javanicus, Rhizopus oryzae*, or *Rhizopus delemar*, for example the product Lipase D Amano 2000™ (also designated Lipase D2™) which is commercially available from Amano Pharmaceuticals, Japan.

In further particular embodiments, the lipase is a recombinantly produced microbial lipase, for example derived from a fungus such as *Humicola* or *Rhizomucor*, from a yeast such as *Candida*, or from a bacterium such as *Pseudomonas*. In a preferred embodiment, the lipase is derived from a strain of *Humicola lanuginosa* or *Rhizomucor miehei*.

The *Humicola lanuginosa* (synonym *Thermomyces lanuginosus*) lipase (SEQ ID NO: 9) is described in EP 305216, and particular lipase variants are described in, for example, WO 92/05249, WO 92/19726, WO 94/25577, WO 95/22615, WO 97/04079, WO 97/07202, WO 99/42566, WO 00/32758, WO 00/60063, WO 01/83770, WO 02/055679, and WO 02/066622. A preferred lipase variant is a lipase comprising amino acids 1-269, or 2-269, of SEQ ID NO: 8, such as the following: (i) amino acids +1 to +269 of SEQ ID NO: 8, (ii) amino acids −5 to +269 of SEQ ID NO: 8, (iii) amino acids −4 to +269 of SEQ ID NO: 8; (iv) amino acids −3 to +269 of SEQ ID NO: 8; (v) amino acids −2 to +269 of SEQ ID NO: 8; (vi) amino acids −1 to +269 of SEQ ID NO: 8, (vii) amino acids +2 to +269 of SEQ ID NO: 1, as well as (viii) any mixture of two or more of the lipases of (i)-(vii)—and variants thereof. In a particular embodiment, the lipase for use according to the invention is selected from the lipases of (i), (ii), and any mixture of (i) and (ii). Preferred mixtures of (i) and (ii) comprise at least 5%, preferably at least 10%, 20%, 30%, 40%, 50%, 60%, 70%, 80%, 90%, or at least 95% of lipase (i), the percentages being determined by N-terminal sequencing using the Edman method, as described in Example 5 of the PCT application that claims priority from DK patent application no. 2005 00929. Other preferred mixtures are: (a) compositions comprising 35-75%, preferably 40-70%, more preferably 45-65% of lipase (ii); (b) compositions comprising 20-60%, preferably 25-55%, more preferably 30-50%, most preferably 35-47% of lipase (i); (c) compositions comprising up to 30%, preferably up to 25%, more preferably up to 20%, most preferably up to 16% of lipase (vii); and (d) any combination of (a), (b), and/or (c), such as a composition comprising 45-65% of lipase (ii), 35-47% of lipase (i), and up to 16% of lipase (vii).

The lipases of SEQ ID NO: 8 and 9 may, e.g., be prepared on the basis of the basis of the teaching in U.S. Pat. No. 5,869,438 (in which SEQ ID NO: 1 is a DNA sequence encoding the lipase of SEQ ID NO: 9). The lipase of SEQ ID NO: 8 can, e.g., be prepared by recombinant expression in a suitable host cell of a DNA sequence which is a modification of SEQ ID NO:1 of the US patent, the modification reflecting the amino acid differences between SEQ ID NO: 8 and 9 herein. Such modifications can be made by site-directed mutagenesis, as is known in the art.

Still further examples of fungal lipases are the cutinase from *Humicola insolens* which is described in EP 785994, and the phospholipase from *Fusarium oxysporum* which is described in EP 869167. Examples of yeast lipases are lipase A and B from *Candida antarctica* of which lipase A is described in EP 652945, and lipase B is described by, for example, Uppenberg et al in Structure, 2 (1994), 293. An example of a bacterial lipase is the lipase derived from *Pseudomonas cepacia*, which is described in EP 214761.

In a preferred embodiment, the lipase is at least 70% identical to the lipase of SEQ ID NO: 8, or to amino acids 1-269 thereof. In additional preferred embodiments, the degree of identity to SEQ ID NO: 8, or to amino acids 1-269 thereof, is at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In alternative embodiments, the degree of identity to SEQ ID NO: 8, or to amino acids 1-269 thereof, is at least about 50%, 51%, 52%, 53%, 54%, 55%, 56%, 57%, 58%, 59%, 60%, 61%, 62%, 63%, 64%, 65%, 66%, 67%, 68%, or at least 69%.

In a still further preferred embodiment, the lipase, like the mammalian pancreatic lipase, is a 1,3-position specific lipase.

For the purposes of the present invention particularly preferred combinations of enzymes are the following: (i) The protease of amino acids 1-274 of SEQ ID NO: 5 in combination with an amylase comprising amino acids 1-481 of SEQ ID NO: 1 (such as amino acids 1-481, 1-484, 1-486, or 1-513 thereof); (ii) the protease of amino acids 1-274 of SEQ ID NO: 5 in combination with the amylase of SEQ ID NO: 2; (iii) the protease of amino acids 1-274 of SEQ ID NO: 5 in combination with the amylase of SEQ ID NO: 3; (iv) the protease of amino acids 1-188 of SEQ ID NO: 6 in combination with an amylase comprising amino acids 1-481 of SEQ ID NO: 1 (such as amino acids 1-481, 1-484, 1-486, or 1-513 thereof); (v) the protease of amino acids 1-188 of SEQ ID NO: 6 in combination with the amylase of SEQ ID NO: 2; (vi) the protease of amino acids 1-188 of SEQ ID NO: 6 in combination with the amylase of SEQ ID NO: 3; (vii) a lipase comprising amino acids 1-269, or 2-269, of SEQ ID NO: 8 in combination with an amylase comprising amino acids 1-481 of SEQ ID NO: 1 (such as amino acids 1-481, 1-484, 1-486, or 1-513 thereof); (viii) a lipase comprising amino acids 1-269, or 2-269, of SEQ ID NO: 8 in combination with the amylase of SEQ ID NO: 2; (ix) a lipase comprising amino acids 1-269, or 2-269, of SEQ ID NO: 8 in combination with the amylase of SEQ ID NO: 3; (x) the protease of amino acids 1-274 of SEQ ID NO: 5 in combination with an amylase comprising amino acids 1-481 of SEQ ID NO: 1 (such as amino acids 1-481, 1-484, 1-486, or 1-513 thereof) and a lipase comprising amino acids 1-269, or 2-269, of SEQ ID NO: 8; (xi) the protease of amino acids 1-274 of SEQ ID NO: 5 in combination with the amylase of SEQ ID NO: 2 and a lipase comprising amino acids 1-269, or 2-269, of SEQ ID NO: 8; (xii) the protease of amino acids 1-274 of SEQ ID NO: 5 in combination with the amylase of SEQ ID NO: 3 and a lipase comprising amino acids 1-269, or 2-269, of SEQ ID NO: 8); (xiii) the protease of amino acids 1-188 of SEQ ID NO: 6 in combination with an amylase comprising amino acids 1-481 of SEQ ID NO: 1 (such as amino acids 1-481, 1-484, 1-486, or 1-513 thereof) and a lipase comprising amino acids 1-269, or 2-269, of SEQ ID NO: 8; (xiv) the protease of amino acids 1-188 of SEQ ID NO: 6 the amylase of SEQ ID NO: 2 and a lipase comprising amino acids 1-269, or 2-269, of SEQ ID NO: 8; (xv) the protease of amino acids 1-188 of SEQ ID NO: 6 in combination with the amylase of SEQ ID NO: 3 and a lipase comprising amino acids 1-269, or 2-269, of SEQ ID NO: 8; (xvi) a protease having amino acids 1-188 of SEQ ID NO: 7 in combination with an amylase comprising amino acids 1-481 of SEQ ID NO: 1 (such as amino acids 1-481, 1-484, 1-486, or 1-513 thereof); (xvii) a protease having amino acids 1-188 of SEQ ID NO: 7 in combination with an amylase having amino acids 1-481 of SEQ ID NO: 2; (xviii) a protease having amino acids 1-188 of SEQ ID NO: 7 in combination with an amylase having amino acids 1-483 of SEQ ID NO: 3; (xix) a protease having amino acids 1-188 of SEQ ID NO: 7 in combination with an amylase comprising amino acids 1-481 of SEQ ID NO: 1 (such as amino acids 1-481, 1-484, 1-486, or 1-513 thereof) and a lipase comprising amino acids 1-269, or 2-269, of SEQ ID NO: 8; (xx) a protease having amino acids 1-188 of SEQ ID NO: 7 in combination with an amylase having amino acids 1-481 of SEQ ID NO: 2 and a lipase comprising amino acids 1-269, or 2-269, of SEQ ID NO: 8; and (xi) a protease having amino acids 1-188 of SEQ ID NO: 7 in combination with an amylase having amino acids 1-483 of SEQ ID NO: 3 and a lipase comprising amino acids 1-269, or 2-269, of SEQ ID NO: 8.

Accordingly, one embodiment of the present invention relates to an amylase in combination with a lipase and/or a protease according to claim 4 or 5, wherein the amylase is an amylase selected from the group consisting of a) an amylase comprising amino acids 1-481 of SEQ ID NO: 1, b) an amylase having amino acids 1-481 of SEQ ID NO: 2, and c) an amylase having amino acids 1-483 of SEQ ID NO: 3; (ii) the lipase comprises amino acids 2-269 of SEQ ID NO: 8; (iii) the protease is a protease selected from the group consisting of a) a protease having amino acids 1-274 of SEQ ID NO: 5, b) a protease having amino acids 1-188 of SEQ ID NO: 6, and c) a protease having amino acids 1-188 of SEQ ID NO: 7.

Other preferred combinations of enzymes are the following: (i) A protease having at least 50% identity to amino acids 1-274 of SEQ ID NO: 5 in combination with an amylase having at least 50% identity to amino acids 1-481 of SEQ ID NO: 1; (ii) a protease having at least 50% identity to amino acids 1-274 of SEQ ID NO: 5 in combination with an amylase having at least 50% identity to amino acids 1-481 of SEQ ID NO: 2; (iii) a protease having at least 50% identity to amino acids 1-274 of SEQ ID NO: 5 in combination with an amylase having at least 50% identity to amino acids 1-483 of SEQ ID NO: 3; (iv) a protease having at least 50% identity to amino acids 1-188 of SEQ ID NO: 6 in combination with an amylase having at least 50% identity to amino acids 1-481 of SEQ ID NO: 1; (v) a protease having at least 50% identity to amino acids 1-188 of SEQ ID NO: 6 in combination with an amylase having at least 50% identity to amino acids 1-481 of SEQ ID NO: 2; (vi) a protease having at least 50% identity to amino acids 1-188 of SEQ ID NO: 6 in combination with an amylase having at least 50% identity to amino acids 1-483 of SEQ ID NO: 3; (vii) a lipase having at least 50% identity to amino acids 1-269 of SEQ ID NO: 8 in combination with an amylase having at least 50% identity to amino acids 1-481 of SEQ ID NO: 1; (viii) a lipase having at least 50% identity to amino acids 1-269 of SEQ ID NO: 8 in combination with an amylase having at least 50% identity to SEQ ID NO: 2; (ix) a lipase having at least 50% identity to amino acids 1-269 of SEQ ID NO: 8 in combination with an amylase having at least 50% identity to amino acids 1-483 of SEQ ID NO: 3; (x) a protease having at least 50% identity to amino acids 1-274 of SEQ ID NO: 5 in combination with an amylase having at least 50% identity to amino acids 1-481 of SEQ ID NO: 1 and a lipase having at least 50% identity to amino acids 1-269 of SEQ ID NO: 8; (xi) a protease having at least 50% identity to amino acids 1-274 of SEQ ID NO: 5 in combination with an amylase having at least 50% identity to amino acids 1-481 of SEQ ID NO: 2 and a lipase having at least 50% identity to amino acids 1-269 of SEQ ID NO: 8; (xii) a protease having at least 50% identity to amino acids 1-274 of SEQ ID NO: 5 in combination with an amylase having at least 50% identity to amino acids 1-483 of SEQ ID NO: 3 and a lipase having at least 50% identity to amino acids 1-269 of SEQ ID NO: 8); (xiii) a protease having at least 50% identity to amino acids 1-188 of SEQ ID NO: 6 in combination with an amylase having at least 50% identity to amino acids 1-481 of SEQ ID NO: 1 and a lipase having at least 50% identity to amino acids 1-269 of SEQ ID NO: 8; (xiv) a protease having at least 50% identity to amino acids 1-188 of SEQ ID NO: 6 in combination with an amylase having at least 50% identity to amino acids 1-481 of SEQ ID NO: 2 and a lipase having at least 50% identity to amino acids 1-269 of SEQ ID NO: 8; (xv) a protease having at least 50% identity to amino acids 1-188 of SEQ ID NO: 6 in combination with an amylase having at least 50% identity to amino acids 1-483 of SEQ ID NO: 3 and a lipase having at least 50% identity to amino acids 1-269 of SEQ ID NO: 8; (xvi) a protease having at least 50% identity to amino acids 1-188 of SEQ ID NO: 7 in combination with an amylase having at least 50% identity to amino acids 1-481 of SEQ ID NO: 1; (xvii) a protease having at least 50% identity to amino acids 1-188 of SEQ ID NO: 7 in combination with an amylase having at least 50% identity to amino acids 1-481 of SEQ ID NO: 2; (xviii) a protease having at least 50% identity to amino acids 1-188 of SEQ ID NO: 7 in combination with an amylase having at least 50% identity to amino acids 1-483 of SEQ ID NO: 3; (xix) a protease having at least 50% identity to amino acids 1-188 of SEQ ID NO: 7 in combination with an amylase having at least 50% identity to amino acids 1-481 of SEQ ID NO: 1 and a lipase having at least 50% identity to amino acids 1-269 of SEQ ID NO: 8; (xx) a protease having at least 50% identity to amino acids 1-188 of SEQ ID NO: 7 in combination with an amylase having at least 50% identity to amino acids 1-481 of SEQ ID NO: 2 and a lipase having at least 50% identity to amino acids 1-269 of SEQ ID NO: 8; and (xi) a protease having at least 50% identity to amino acids 1-188 of SEQ ID NO: 7 in combination with an amylase having at least 50% identity to amino acids 1-483 of SEQ ID NO: 3 and a lipase having at least 50% identity to amino acids 1-269 of SEQ ID NO: 8. In preferred embodiments of (i)-(xi), each degree of identity is, independently, at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%.

Accordingly, one embodiment of the invention relates to an amylase in combination with a lipase and/or a protease according to claim 4 or 5, wherein (i) the amylase is an amylase as defined herein; (ii) the lipase has at least 70% identity to a lipase having amino acids 1-269 of SEQ ID NO: 8; (ii) the protease has at least 70% identity to a protease selected from the group consisting of a) a protease having amino acids 1-274 of SEQ ID NO: 5, b) a protease having amino acids 1-188 of SEQ ID NO: 6, and c) a protease having amino acids 1-188 of SEQ ID NO: 7.

Generally, the amylase, protease, and lipase enzymes (hereinafter "the enzyme(s)") of the invention may be natural or wild-type enzymes obtained from animals, in particular mammals, for example human or swine enzymes; from plants, or from microorganisms, but also any mutants, variants, fragments etc. thereof exhibiting the desired enzyme activity, as well as synthetic enzymes, such as shuffled, hybrid, or chimeric enzymes, and consensus enzymes.

In a specific embodiment, the enzyme(s) are low-allergenic variants, designed to invoke a reduced immunological response when exposed to animals, including man. The term immunological response is to be understood as any reaction by the immune system of an animal exposed to the enzyme(s). One type of immunological response is an allergic response leading to increased levels of IgE in the exposed animal. Low-allergenic variants may be prepared using techniques known in the art. For example the enzyme(s) may be conjugated with polymer moieties shielding portions or epitopes of the enzyme(s) involved in an immunological response. Conjugation with polymers may involve in vitro chemical coupling of polymer to the enzyme(s), e.g. as described in WO 96/17929, WO 98/30682, WO 98/35026, and/or WO 99/00489. Conjugation may in addition or alternatively thereto involve in vivo coupling of polymers to the enzyme(s). Such conjugation may be achieved by genetic engineering of the nucleotide sequence encoding the enzyme(s), inserting consensus sequences encoding additional glycosylation sites in the enzyme(s) and expressing the enzyme(s) in a host capable of glycosylating the enzyme(s), see e.g. WO 00/26354. Another way of providing low-allergenic variants is genetic engineering of the nucleotide sequence encoding the enzyme(s) so as to cause the enzymes to self-oligomerize, effecting that enzyme monomers may shield the epitopes of other enzyme monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the enzyme(s) by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

In particular embodiments, the enzyme(s) are (i) stable at pH 2-8, preferably also at pH 3-7, more preferably at pH 4-6; (ii) active at pH 4-9, preferably 4-8; (iii) stable against degradation by pepsin and other digestive proteases (such as pancreas proteases, i.e., mainly trypsin and chymotrypsin); and/or (iv) stable and/or active in the presence of bile salts.

In a preferred embodiment, the amylase of the invention has an activity at pH 7.0 and 37° C. of at least 35% relative to the activity at the pH-optimum and 37° C. More preferably, the activity at pH 7.0 and 37° C. is at least 40, 45, 50, 55, 60, 65, 70, or at least 75% of the activity at the pH-optimum and 37° C. (cf. Table 2 of Example 3).

In another preferred embodiment, the amylase of the invention has an activity at pH 7.0 and 37° C. and in the presence of 5 mM bile salts of at least 25% relative to the activity at the pH-optimum and 37° C. in the absence of bile salts. More preferably, the activity at pH 7.0 and 37° C. and in the presence of 5 mM bile salts is at least 30, 35, 40, 45, 50, 55, 60, or at least 65% of the activity at the pH-optimum and 37° C. in the absence of bile salts (cf. Table 3 of Example 3)

In a still further preferred embodiment, the specific activity of the amylase of the invention, at pH 7.0 and 37° C., is at least 10%, more preferably at least 15, 20, 25, 30, 35, 40, 45, 50, 55, 60, 65, or at least 70%, relative to the specific activity of the amylase of SEQ ID NO: 1 at pH 5.0 and 37° C. (cf. Table 4 of Example 3).

In another preferred embodiment, the specific activity of the amylase of the invention, at pH 7.0 and 37° C. and in the presence of 5 mM bile salts, is at least 10%, more preferably at least 15, 20, 25, 30, 35, 40, 45, 50, 55, 60, 65, 70, or at least 75%, relative to the specific activity of the amylase of SEQ ID NO: 1 at pH 5.0 and 37° C. and in the presence of 5 mM bile salts (cf. Table 5 of Example 3).

The activities referred to in the above preferred embodiments may suitably be determined using a reducing sugar assay, e.g. as described in Example 3, using preferably waxy corn as a substrate. A detailed procedure is described in Example 3.

In a further, independent, particular embodiment, the amylase of the invention has a starch degradation profile with one or more of the following characteristic features: (i) DP1 is detected as a degradation product; (i) the DP4 amount is lower than the amount of DP5; (iii) the DP4 amount is lower than the amount of DP6; and/or (iv) the amount of DP5 and/or DP6 is higher than the amount of DP1. The monomer DP1 is preferably glucose, and the DP2-DP6 products are dimers-hexamers, respectively, of glucose.

The degradation profile may be determined using HPLC as described in Example 4, i.e. after having incubated for 24 hours at a temperature of 60 or 37° C., at a pH of 6.0 or 5.5, preferably using waxy corn as a substrate, more preferably in the presence of $Ca^{2+}$.

The term "in combination with" refers to the combined use according to the invention of the protease, lipase, and/or amylase. The combined use can be simultaneous, overlapping, or sequential, these three terms being generally interpreted in the light of the prescription made by the physician.

The term "simultaneous" refers to circumstances under which the enzymes are active at the same time, for example when they are administered at the same time as one or more separate pharmaceutical products, or if they are administered in one and the same pharmaceutical composition.

The term "sequential" refers to such instances where one and/or two of the enzymes are acting first, and the second and/or third enzyme subsequently. A sequential action can be obtained by administering the enzymes in question as separate pharmaceutical formulations with desired intervals, or as one pharmaceutical composition in which the enzymes in question are differently formulated (compartmentalized), for example with a view to obtaining a different release time, providing an improved product stability, or to optimizing the enzyme dosage.

The term "overlapping" refers to such instances where the enzyme activity periods are neither completely simultaneous nor completely sequential, viz. there is a certain period in which the enzymes are both, or all, active.

The term "a", for example when used in the context of the enzyme(s) of the invention, means at least one. In particular embodiments, "a" means "one or more," or "at least one", which again means one, two, three, four, five etc.

The relatedness between two amino acid sequences is described by the parameter "identity".

For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1-481 of SEQ ID NO: 1) and a different amino acid sequence ("foreign sequence"; e.g. amino acids 1-514 of SEQ ID NO: 12) is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap (in the alignment example below this is represented by "|"). The length of a sequence is the number of amino acid residues in the sequence (e.g. the length of SEQ ID NO: 1 is 481).

In the, purely hypothetical, alignment example below, the overlap is the amino acid sequence "HTWGER-NL" of Sequence 1; or the amino acid sequence "HGWGEDANL" of Sequence 2. In the example a gap is indicated by a "-".
Hypothetical Alignment Example:

```
Sequence 1:      ACMSHTWGER-NL
                     | |||| ||
Sequence 2:          HGWGEDANLAMNPS
```

Accordingly, the percentage of identity of Sequence 1 to Sequence 2 is 6/12=0.5, corresponding to 50%.

In a particular embodiment, the percentage of identity of an amino acid sequence of a polypeptide with, or to, amino acids 1-481 of SEQ ID NO: 1 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage. The percentage of identity to, or with, other sequences of the invention such as amino acids 1-481 of SEQ ID NO: 2, or 1-483 of SEQ ID NO: 3, is calculated in an analogous way.

In the alternative, the degree of identity between two amino acid sequences may be determined by the program "align" which is a Needleman-Wunsch alignment (i.e. a global alignment). The sequences are aligned by the program, using the default scoring matrix BLOSUM50. The penalty for the first residue of a gap is 12, and for further residues of a gap the penalties are 2. The Needleman-Wunsch algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. "Align" is part of the FASTA package version v20u6 (see W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA," Methods in Enzymology 183:63-98).

The degree of identity between a sample, or test, sequence of any of the enzyme(s) of the invention and a specified sequence may be determined as follows: The two sequences are aligned using the program "align." The number of perfect matches ("N-perfect-match") in the alignment is determined (a perfect match means same amino acid residue in same position of the alignment). The common length of the two aligned sequences is also determined, viz. the total number of amino acids in the alignment (the overlap), including trailing and leading gaps created by the alignment, if any ("N-overlap"). The degree of identity is calculated as the ratio between "N-perfect-match" and "N-overlap" (for conversion to percentage identity, multiply by 100).

In an alternative embodiment, the degree of identity between the sample, or test, sequence and a specified sequence may be determined as follows: The sequences are aligned using the program "align." The number of perfect matches ("N-perfect-match") in the alignment is determined (a perfect match means same amino acid residue in same position of the alignment). The length of the sample sequence (the number of amino acid residues) is determined ("N-sample"). The degree of identity is calculated as the ratio between "N-perfect-match" and "N-sample" (for conversion to percentage identity, multiply by 100).

In another alternative embodiment, the degree of identity between the sample, or test, sequence and a specified sequence may be determined as follows: The sequences are aligned using the program "align." The number of perfect matches ("N-perfect-match") in the alignment is determined (a perfect match means same amino acid residue in same position of the alignment). The length of the specified sequence (the number of amino acid residues) is determined ("N-specified"). The degree of identity is calculated as the ratio between "N-perfect-match" and "N-specified" (for conversion to percentage identity, multiply by 100).

Preferably, the overlap is at least 20% of the specified sequence ("N-overlap" as defined above, divided by the number of the amino acids in the specified sequence ("N-specified"), and multiplied by 100), more preferably at least 25%, 30%, 35%, 40%, 45%, 50%, 55%, 60%, 65%, 70%, 75%, 80%, 85%, 90%, or at least 95%. This means that at least 20% (preferably 25-95%) of the amino acids of the specified sequence end up being included in the overlap, when the sample sequence is aligned to the specified sequence.

In the alternative, the overlap is at least 20% of the specified sequence ("N-overlap" as defined above, divided by "N-sample" as defined above, and multiplied by 100), more preferably at least 25%, 30%, 35%, 40%, 45%, 50%, 55%, 60%, 65%, 70%, 75%, 80%, 85%, 90%, or at least 95%. This means that at least 20% (preferably 25-95%) of the amino acids of the sample sequence end up being included in the overlap, when aligned against the specified sequence.

The activity of the enzyme(s) of the invention can be measured using any suitable assay. Generally, assay-pH and assay-temperature may be adapted to the enzyme in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Preferred pH values and temperatures are in the physiological range, such as pH values of 4, 5, 6, 7, or 8, and temperatures of 30, 35, 37, or 40° C.

Suitable assays are described in the experimental part, and in DK patent application no. 2005 00929 and 2005 00930 as well as the corresponding PCT-applications.

Other examples are the Ph. Eur. assays for protease, lipase and amylase activity.

Medicament

In the present context, the term "medicament" means a compound, or mixture of compounds, that treats, prevents and/or alleviates the symptoms of disease, preferably treats and/or alleviates. The medicament may be prescribed by a physician, or it may be an over-the-counter product.

Pharmaceutical Compositions

Isolation, purification, and concentration of the enzyme(s) of the invention may be carried out by conventional means. For example, they may be recovered from a fermentation broth by conventional procedures including, but not limited to, centrifugation, filtration, extraction, spray-drying, evaporation, or precipitation, and further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulphate precipitation), SDS-PAGE, or extraction (see, e.g., Protein Purification, J.-C. Janson and Lars Ryden, editors, VCH Publishers, New York, 1989).

For example, DNA encoding the amylase of the invention (such as SEQ ID NOs: 13-16 encoding SEQ ID NOs: 1-4, respectively) may be recombinantly expressed in a *Bacillus* host cell as is known in the art, and purified from the fermentation liquid by process steps like centrifugation, filtration, ultrafiltration and, if desired, germ-filtration. Additional, optional, process steps include various kinds of chromatography like, e.g., ion-exchange chromatography and hydrophobic interaction chromatography. A suitable hydrophobic column material is butyl or phenyl, and such columns are commercially available, e.g. from Pharmacia. The pI of the amylases of SEQ ID NO: 1, 2, and 3 are 5.7, 7.3, and 8.8, respectively, and the molecular weights approximately 55 kDa by SDS-PAGE for all three amylases.

In a particular embodiment, concentrated solid or liquid preparations of each of the enzyme(s) are prepared separately. These concentrates may also, at least in part, be separately formulated, as explained in more detail below.

In a further particular embodiment, the enzyme(s) are incorporated in the pharmaceutical compositions of the invention in the form of solid concentrates. The enzyme(s) can be brought into the solid state by various methods as is known in the art. For example, the solid state can be either crystalline, where the enzyme molecules are arranged in a highly ordered form, or a precipitate, where the enzyme molecules are arranged in a less ordered, or disordered, form.

Crystallization may, for example, be carried out at a pH close to the pI of the enzyme(s) and at low conductivity, for example 10 mS/cm or less, as described in EP 691982.

Various precipitation methods are known in the art, including precipitation with salts, such as ammonium sulphate, and/or sodium sulphate; with organic solvents, such as ethanol, and/or isopropanol; or with polymers, such as PEG (Poly Ethylene Glycol). In the alternative, the enzyme(s) can be precipitated from a solution by removing the solvent (typically water) by various methods known in the art, e.g. lyophilization, evaporation (for example at reduced pressure), and/or spray drying.

In a further particular embodiment, the solid concentrate of the enzyme(s) has a content of active enzyme protein of at least 50% (w/w) by reference to the total protein content of the solid concentrate. In still further particular embodiments, the content of active enzyme protein, relative to the total protein content of the solid concentrate is at least 55, 60, 65, 70, 75, 80, 85, 90, or at least 95% (w/w). The protein content can be measured as is known in the art, for example by densitometer scanning of coomassie-stained SDS-PAGE gels, e.g. using a GS-800 calibrated densitometer from BIO-RAD; by using a commercial kit, such as Protein Assay ESL, order no. 1767003, which is commercially available from Roche, or on the basis of the method described in Example 8 of WO 01/58276.

Preferably, the amylase enzyme protein constitutes at least 50%, more preferably at least 55, 60, 65, 70, 75, 80, 85, 90, 92, 94, 95, 96, or at least 97% of the protein spectrum of the solid lipase concentrate for use according to the invention, as measured by densitometer scanning of a coomassie-stained SDS-PAGE gel.

A pharmaceutical composition of the invention comprises the enzyme(s), preferably in the form of concentrated enzyme preparations, more preferably solid concentrates, together with at least one pharmaceutically acceptable auxiliary, or subsidiary, material such as (i) at least one carrier and/or excipient; or (ii) at least one carrier, excipient, diluent, and/or adjuvant. Non-limiting examples of, optional, other ingredients, all pharmaceutically acceptable, are disintegrators, lubricants, buffering agents, moisturizing agents, preservatives, flavouring agents, solvents, solubilizing agents, suspending agents, emulsifiers, stabilizers, propellants, and vehicles.

Generally, depending i.a. on the medical indication in question, the composition of the invention may be designed for all manners of administration known in the art, preferably including enteral administration (through the alimentary canal). Thus, the composition may be in solid, semi-solid, liquid, or gaseous form, such as tablets, capsules, powders, granules, microspheres, ointments, creams, foams, solutions, suppositories, injections, inhalants, gels, microspheres, lotions, and aerosols. The medical practitioner will know to select the most suitable route of administration and of course avoid potentially dangerous or otherwise disadvantageous administration routes.

The following methods and auxiliary materials are therefore also merely exemplary and are in no way limiting.

For solid oral preparations, the enzyme(s) can be used alone or in combination with appropriate additives to make pellets, micropellets, tablets, microtablets, powders, granules or capsules, for example, with conventional carriers, such as lactose, mannitol, corn starch, or potato starch; with excipients or binders, such as crystalline, or microcrystalline, cellulose, cellulose derivatives, acacia, corn starch, or gelatins; with disintegrators, such as corn starch, potato starch, or sodium carboxymethylcellulose; with lubricants, such as carnauba wax, white wax, shellac, waterless colloid silica, polyethylene glycol (PEGs, also known under the term macrogol) from 1500 to 20000, in particular PEG 4000, PEG 6000, PEG 8000, povidone, talc, monolein, or magnesium stearate; and if desired, with diluents, adjuvants, buffering agents, moistening agents, preservatives such as methylparahydroxybenzoate (E218), colouring agents such as titanium dioxide (E171), and flavouring agents such as saccharose, saccharin, orange oil, lemon oil, and vanillin. Oral preparations are examples of preferred preparations for treatment of the medical indication of PEI.

The enzyme(s) can also, quite generally, be formulated into liquid oral preparations, by dissolving, suspending, or emulsifying them in an aqueous solvent such as water, or in non-aqueous solvents such as vegetable or other similar oils, synthetic aliphatic acid glycerides, esters of higher aliphatic acids, propylene glycol, polyethylene glycol such as PEG 4000, or lower alcohols such as linear or ramified C1-C4 alcohols, for example 2-propanol; and if desired, with conventional subsidiary materials or additives such as solubilizers, adjuvants, diluents, isotonic agents, suspending agents, emulsifying agents, stabilizers, and preservatives.

Furthermore, the enzyme(s) can generally be made into suppositories for rectal administration by mixing with a variety of bases such as emulsifying bases or water-soluble bases. The suppository can include vehicles such as cocoa butter, carbowaxes and polyethylene glycols, which melt at body temperature, yet are solidified at room temperature.

The use of liposomes as a delivery vehicle is another method of possible general interest. The lipids may be any useful combination of known liposome forming lipids, including cationic or zwitterionic lipids, such as phosphatidylcholine. The remaining lipid will normally be neutral or acidic lipids, such as cholesterol, phosphatidyl serine, phosphatidyl glycerol, and the like. For preparing the liposomes, the procedure described by Kato et al. (1991) J. Biol. Chem. 266:3361 may be used.

Unit dosage forms for oral or rectal administration such as syrups, elixirs, powders, and suspensions may be provided wherein each dosage unit, for example, teaspoonful, tablespoonful, capsule, tablet or suppository, contains a predetermined amount of the enzyme(s). Similarly, unit dosage forms for injection or intravenous administration may comprise the enzyme(s) in a composition as a solution in sterile water, normal saline, or another pharmaceutically acceptable carrier.

The term "unit dosage form", as used herein, refers to physically discrete units suitable as unitary dosages for human and animal subjects, each unit containing a predetermined quantity of enzyme(s) in an amount sufficient to produce the desired effect.

In a particular embodiment, the pharmaceutical composition of the invention is for enteral, preferably oral, administration.

In further particular embodiments, the oral composition is (i) a liquid composition containing crystals of the enzyme(s); (ii) a liquid suspension of sediments of (highly) purified enzyme(s); (iii) a gel containing the enzyme(s) in solid or solubilized form; (iv) a liquid suspension of immobilized enzyme(s) or of enzymes adsorbed to particles and the like; or (v) a solid composition in the form of enzyme(s)-containing powder, pellets, granules, or microspheres, if desired in the form of tablets, capsules, or the like, that are optionally coated, for example with an acid-stable coating.

In another particular embodiment of the composition, the enzyme(s) are compartmentalized, viz. separated from each other, for example by means of separate coatings.

In a still further particular embodiment of the composition, the protease is separated from other enzyme components of the composition, such as the lipase, and/or the amylase.

The dosage of the enzyme(s) will vary widely, depending on the specific enzyme(s) to be administered, the frequency of administration, the manner of administration, the severity of the symptoms, and the susceptibility of the subject to side effects, and the like. Some of the specific enzymes may be more potent than others.

Examples of solid oral preparations of the enzyme(s) of the invention comprise: (i) an amylase of at least 50% identity to (i) amino acids 1-481 of SEQ ID NO: 1, (ii) amino acids 1-481 of SEQ ID NO: 2, and/or (iii) amino acids 1-483 of SEQ ID NO: 3; (ii) a protease having at least 70% identity to a protease selected from the group consisting of a) a protease having amino acids 1-274 of SEQ ID NO: 5, b) a protease having amino acids 1-188 of SEQ ID NO: 6, and c) a protease having amino acids 1-188 of SEQ ID NO: 7; and/or (iii) a lipase having at least 70% identity to a lipase having amino acids 1-269 of SEQ ID NO: 8; wherein preferably the anticipated daily clinical dosages of the enzymes of (i), (ii), and (iii) are as follows (all in mg enzyme protein per kg of bodyweight (bw)): For the amylase of (i): 0.001-250, 0.005-100, 0.01-50, or 0.05-10 mg/kg bw; for the protease of (ii): 0.005-500, 0.01-250, 0.05-100, or 0.1-50 mg/kg bw; for the lipase of (iii): 0.01-1000, 0.05-500, 0.1-250, or 0.5-100 mg/kg bw.

A preferred example of solid oral preparations of the enzyme(s) of the invention comprise: (i) an amylase comprising amino acids 1-481 of SEQ ID NO: 1, (ii) a protease comprising amino acids 1-274 of SEQ ID NO: 5, and/or (i) a lipase comprising amino acids 2-269 of SEQ ID NO: 8.

Examples of anticipated daily clinical dosages of the enzymes of (i), (ii), and (iii) are as follows (all in mg enzyme protein per kg of bodyweight (bw)): For the amylase of (i): 0.01-50, 0.05-10, or 0.1-5 mg/kg bw; for the protease of (ii): 0.05-100, 0.1-50, or 0.5-25 mg/kg bw; for the lipase of (iii): 0.1-250, 0.5-100, or 1-50 mg/kg bw.

The amide (peptide) bonds, as well as the amino and carboxy termini, may be modified for greater stability on oral administration. For example, the carboxy terminus may be amidated.

Particular embodiments of pharmaceutical compositions of the invention, suitable for the treatment of digestive disorders, PEI, pancreatitis, cystic fibrosis, diabetes type I, and/or diabetes type II, may be prepared by incorporating the enzyme(s) of the invention into pellets. The pellets may generally comprise from 10-90% (w/w, relative to the dry weight of the resulting pellets) of a physiologically acceptable organic polymer, from 10-90% (w/w, relative to the dry weight of the resulting pellets) of cellulose or a cellulose derivative, and from 80-20% (w/w, relative to the dry weight of the resulting pellets) of the enzyme(s), the total amount of organic polymer, cellulose or cellulose derivative and enzyme(s) making up to 100% in each case.

The physiologically acceptable organic polymer can be selected from the group consisting of polyethylene glycol 1500, polyethylene glycol 2000, polyethylene glycol 3000, polyethylene glycol 4000, polyethylene glycol 6000, polyethylene glycol 8000, polyethylene glycol 10000, polyethylene glycol 20000, hydroxypropyl methylcellulose, polyoxyethylen, copolymers of polyoxyethylen-polyoxypropylen and mixtures of said organic polymers. Polyethylene glycol 4000 is preferred as physiologically acceptable organic polymer.

The cellulose or a cellulose derivative can e.g. be selected from cellulose, cellulose acetate, cellulose fatty acid ester, cellulose nitrates, cellulose ether, carboxymethyl cellulose, ethyl cellulose, hydroxyethyl cellulose, hydroxypropyl cellulose, methyl cellulose, methyl ethylcellulose and methylhydroxypropyl cellulose. Cellulose, in particular microcrystalline cellulose is preferred as cellulose or cellulose derivative.

The resulting pellets may be coated with a suitable enteric coating, other non functional coating or be used directly without such coating. Further, the resulting pellets may be filled in capsules like hard gelatin capsules or gelatin free capsules of a suitable size for therapy of a disorder or disease as described in more detail above. In an embodiment of the invention, pellets produced from different enzyme types, in particular from lipase, protease and/or amylase may be filled into said capsules. While filling the capsules with the different enzyme types, the dosing of the single enzyme types (viz. lipase, protease or amylase) may be adapted to specific needs of a certain indication group or a certain patient subgroup by adding a specified amount of any of lipase, protease and/or amylase to the capsules, i.e. capsules may be produced which vary in their specific ratios of lipase:protease:amylase.

Preferred pharmaceutical compositions of the lipase of the invention are described in WO 2005/092370, in particular formulations comprising the preferred excipients mentioned therein. In a particularly preferred embodiment, the pharmaceutical composition comprises a macrogolglyceride mixture of mono-, di- and tri-acylglycerides and polyethylene glycol (PEG) mono- and di-esters of aliphatic C6-C22 carboxylic acids, and also possibly small proportions of glycerol and free polyethylene glycol.

The polyethylene glycol (PEG) contained in the macrogolglyceride mixtures is preferably PEG which has on average 6 to at most 40 ethylene oxide units per molecule or a molecular weight of between 200 and 2000.

One further aspect of the invention provides for the pharmaceutical composition of the enzyme(s) of the invention to comprise a system consisting of surfactant, co-surfactant and lipophilic phase, the system having an HLB value (Hydrophilic-Lipophilic Balance) greater than or equal to 10 and a melting point greater than or equal to 30° C. In a preferred embodiment, the system has an HLB value of 10 to 16, preferably of 12 to 15, and has a melting point of between 30 and 600° C., preferably between 40 and 500° C. In particular, the system characterised by HLB value and melting point is a mixture of mono-, di- and triacylgylcerides and mono- and diesters of polyethylene glycol (PEG) with aliphatic carboxylic acids with 8 to 20, preferably 8 to 18, carbon atoms, whereby the polyethylene glycol preferably has about 6 to about 32 ethylene oxide units per molecule, and the system optionally contains free glycerin and/or free polyethylene glycol. The HLB value of such a system is preferably regulated by the chain length of the PEG. The melting point of such a system is regulated by the chain length of the fatty acids, the chain length of the PEG and the degree of saturation of the fatty-acid chains, and hence the starting oil for the preparation of the macrogolglyceride mixture.

"Aliphatic C8-C18 carboxylic acids" designates mixtures in which caprylic acid (C8), capric acid (C10), lauric acid (C12), myristic acid (C14), palmitic acid (C16) and stearic acid (C18) are contained in a significant and variable proportion, if these acids are saturated, and the corresponding unsaturated C8-C18 carboxylic acids. The proportions of these fatty acids may vary according to the starting oils.

Such a mixture of mono-, di- and triacylgylcerides and mono- and diesters of polyethylene glycol (PEG) with aliphatic carboxylic acids with 8 to 18 carbon atoms can for example be obtained by a reaction between a polyethylene glycol with a molecular weight of between 200 and 1500 and a starting oil, the starting oil consisting of a triglyceride mixture with fatty acids which are selected from the group containing caprylic acid, capric acid, lauric acid, myristic acid, palmitic acid, stearic acid, oleic acid and linolenic acid, individually or as a mixture. Optionally, the product of such a reaction may also contain small proportions of glycerin and free polyethylene glycol.

Such mixtures are commercially available for example under the trade name Gelucire®. One advantageous embodiment of the invention provides that, of the products known under the trade name Gelucire®, in particular "Gelucire® 50/13" and/or "Gelucire®) 44/14" represent suitable mixtures for use in the pharmaceutical preparations according to the invention.

Gelucire® 50/13 is a mixture with mono-, di- and triacylglycerides and mono- and diesters of polyethylene glycol, with palmitic acid (C16) and stearic acid (C18) at 40% to 50% and 48% to 58%, respectively making up the major proportion of bound fatty acids. The proportion of caprylic acid (C8) and capric acid (C10) is less than 3% in each case, and the proportion of lauric acid (C12) and myristic acid (C14) in each case is less than 5%.

Gelucire® 44/14 is a mixture with mono-, di- and triacylgylcerides and mono- and diesters of polyethylene glycol, the respective proportions of palmitic acid (C16) being 4 to 25%, stearic acid (C18) 5 to 35%, caprylic acid (C8) less than 15%, capric acid (C10) less than 12%, lauric acid (C12) 30 to 50% and myristic acid (C14) 5 to 25%. Gelucire® 44/14 can for example be prepared by an alcoholysis/esterification reaction using palm kernel oil and polyethylene glycol 1500.

A preferred embodiment of the present invention provides for a pharmaceutical composition of the enzyme(s) of the invention which comprises a system containing a mixture of mono-, di- and triacyl-glycerides and polyethylene glycol mono- and diesters of aliphatic C8-C18 carboxylic acids and also possibly small proportions of glycerin and free polyethylene glycol, the system having a melting point between 40° C. and 55° C. and an HLB value in the range between 12 and 15. More preferred, the system has a melting point between 44° C. and 50° C. and an HLB value in the range from 13-14. Alternatively, the system has a melting point around 44° C. and an HLB value of 14, or the system has a melting point around 50° C. and an HLB value of 13.

Methods of Treatment

The amylase of the invention, optionally in combination with a lipase, and/or a protease (the enzyme(s) of the invention), is useful in the therapeutic, and/or prophylactic, treatment of various diseases or disorders in animals. The term "animal" includes all animals, and in particular human beings. Examples of animals are non-ruminants, and ruminants, such as sheep, goat, and cattle, e.g. beef cattle, and cow. In a particular embodiment, the animal is a non-ruminant animal. Non-ruminant animals include mono-gastric animals, e.g. pig (including, but not limited to, piglets, growing pigs, and sows); poultry such as turkey, duck and chicken (including but not limited to broiler chicks, layers); young calves; pets such as cat, and dog; and fish (including but not limited to salmon, trout, tilapia, catfish and carps); and crustaceans (including but not limited to shrimps and prawns). In a particular embodiment the animal is a mammal, more in particular a human being.

For example, the enzyme(s) are useful in the treatment of digestive disorders like maldigestion or dyspepsia that are often caused by a deficient production and/or secretion into the gastrointestinal tract of digestive enzymes normally secreted from, i.a., the stomach, and the pancreas.

Further, the enzyme(s) are particularly useful in the treatment of PEI. PEI can be verified using, i.a., the Borgström test (JOP. J Pancreas (Online) 2002; 3(5):116-125), and it may be caused by diseases and conditions such as pancreatic cancer, pancreatic and/or gastric surgery, e.g. total or partial resection of the pancreas, gastrectomy, post gastrointestinal bypass surgery (e.g. Billroth II gastroenterostomy); chronic pancreatitis; Shwachman Diamond Syndrome; ductal obstruction of the pancreas or common bile duct (e.g. from neoplasm); and/or cystic fibrosis (an inherited disease in which a thick mucus blocks the ducts of the pancreas). The enzyme(s) may also be useful in the treatment of acute pancreatitis.

The effect of the enzyme(s) on digestive disorders can be measured as generally described in EP 0600868, in which Example 2 describes an in vitro digestibility test for measuring lipase stability test under gastric conditions, and Example 3 an in vitro digestibility test for lipase activity in the presence of bile salts. Corresponding tests can be set up for the protease and amylase. Also WO 02/060474 discloses suitable tests, for example (1) an in vitro test for measuring lipid digestion in a swine test feed, and (2) an in vivo trial with pancreas insufficient swine in which the digestibility of fat, protein and starch is measured.

In a particular embodiment, the effect of the amylase of the invention is measured using the in vivo screening test for amylase efficacy of Example 2.

As another example, the enzyme(s) are useful in the treatment of Diabetes mellitus type I, and/or type II, in particular for adjuvant treatment in a diabetes therapy of digestive disorders usually accompanying this disease, with a view to diminishing late complications.

The effect on Diabetes mellitus of the enzyme(s) may be determined by one or more of the methods described in WO 00/54799, for example by controlling the level of glycosylated haemoglobin, the blood glucose level, hypoglycaemic attacks, the status of fat-soluble vitamins like vitamins A, D and E, the required daily dosage of insulin, the body-weight index, and hyper glycaemic periods.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Example 1

Enzyme Assays

Amylase, protease and lipase activity may be determined using the FIP assays (Fédération Internationale Pharmaceutique), 1 FIP-unit=1 Ph.Eur.-unit (European Pharmacopoeia). These assays are described in: Federation Internationale Pharmaceutique, Scientific Section International Commission for the standardisation of pharmaceutical enzymes. a) "Pharmaceutical Enzymes," Editors: R. Ruyssen and A. Lauwers, E. Story Scientia, Ghent, Belgium (1978), b) European Pharmacopoeia. See also Deemester et al in Lauwers A, Scharpé S (eds): Pharmaceutical Enzymes, New York, Marcel Dekker, 1997, p. 343-385. Enzyme standards can be procured from the International Commission on Pharmaceutical Enzymes, Centre for Standards, Harelbekestraat 72, B-9000 Ghent.

Amylase FIP Assay

The amylolytic activity of pancreatin was analyzed according to the method published in the European Pharmacopoeia 5.1 against the pancreatin standard supplied by the FIP. For determination of the amylolytic activity of the amylases for use according to the invention, the assay for amylolytic activity of microbial amylases described by the FIP was modified. In principle, starch is hydrolysed by amylase at pH 5.8 and at constant temperature (37.0+/−0.1° C.) in the presence of sodium chloride and calcium chloride. The reducing groups resulting from the hydrolysis react with iodine in alkaline solution and the excess of iodine are titrated with thiosulphate. One unit of amylase is defined as the amount of enzyme, which, under the defined conditions and substrate, hydrolyzes 1 micromol of glycosidic bond per minute.

Reagents

Substrate solution: The substrate is soluble starch (e.g. Merck, No. 101252). The water content of each batch of soluble starch is determined upon opening of the container. To a quantity of soluble starch equivalent to 10.0 g of the dry substrate, add 50 mL of pure (filtration/ion-exchange) water and mix. Add this suspension, whilst stirring continuously, to 800 mL of boiling pure water. Rinse the container several times with successive quantities, each of 10 mL, of pure water and add the washing water to the hot starch solution. Heat to boiling under continuous stirring. Cool to room temperature and dilute to 1000 mL with pure water.

Buffer (acetate) solution pH 5.8 (0.2 mol/L): Dissolve 12 g of acetic acid, 1 g of sodium chloride and 544 mg calcium chloride in about 800 mL of water. Adjust the pH to 5.8 with a sodium hydroxide solution (about 10 N). Dilute to 1000 mL.

Acetic acid, $CH_3COOH$, p.a.
Sodium chloride, NaCl, p.a.
Calcium chloride×$2H_2O$, p.a.
0.25 N sodium hydroxide
1 N hydrochloric acid
0.1 N iodine solution (e.g. Titrisol (Merck 9910), diluted with pure water)
0.1 N sodium thiosulphate solution
Sulphuric acid (p.a.) 20%: to 4 volume parts water add 1 volume part sulphuric acid 96% carefully.
Fungal amylase reference standard FIP (Batch No. 2; 55310 FIP-U/g, Condition 25° C. without calcium chloride).

Quality control suspension (Fungal Amylase reference standard): Dissolve an accurately weighed quantity of the reference standard so that the solution gives a titration volume of thiosulfate, that is between 2 and 4 mL (e.g. weigh about 12-15 mg of the fungal amylase standard and dissolve in 100 ml buffer solution). The quality control suspension is used only for day to day monitoring of the test system.

Test suspension: Dissolve an accurately weighed quantity of the test sample so that the solution gives a titration volume of thiosulfate, that is between 2 and 4 mL.

Procedure

Test sample: For each determination prepare a reaction solution containing 25.0 mL of substrate solution and 10.0 mL of 0.2 M acetate buffer solution in a 300 mL Erlenmeyer flask. Stopper it with a rubber stopper and place it in a water bath at a constant temperature (37.0+/−0.1° C.). As soon as the substrate mixture has reached a constant temperature, start the reaction by adding 2.0 mL of the test suspension. Shake briefly and incubate for exactly 10 minutes at 37° C. Stop the reaction immediately by adding 4 mL of hydrochloric acid. While stirring add 10 mL of 0.1 N iodine solution, 25 mL of 0.25 N sodium hydroxide and, for rinsing the walls, 20 mL of pure water. Allow the mixture to stand in complete darkness for 15 minutes. Add 4 mL of sulphuric acid and titrate the solution with sodium thiosulphate solution using a microburette. Calculate the average of two determinations.

Quality control sample: Determine the activity of the quality control suspension as described for the test sample in duplicate. Use 2.0 mL of the reference suspension.

Blank values: Prepare blank values of the test and reference suspensions. Repeat the procedure as described above but add the 4 mL of 1 N hydrochloric acid before addition of the test and the reference solution.

Calculate the amylase activity in Units per g of test sample using the following equation:

$$\frac{(n_U - n_{UB}) \times 5 \times 1{,}000 \text{ test solution [ml]}}{2 \text{ ml} \times \text{weighted sample [mg]}} = \frac{\text{amylase units}}{\text{[g] test sample}}$$

nU: consumption of 0.1 N sodium thiosulphate [mL] used in the titration of the test suspension;
nUB: consumption of 0.1 N sodium thiosulphate [mL] used in the blank titration of the test suspension;

The measured activity of the monitoring sample (Fungal reference sample) is 97500 U/g, with a Range of Mean+/−3× SD, in particular with a Range of +/−6000 U/g.

Amylase

Alternatively, the following amylase assay can be used:
Substrate: Phadebas tablets (Pharmacia Diagnostics; cross-linked, insoluble, blue-coloured starch polymer, which is mixed with bovine serum albumin and a buffer substance, and manufactured into tablets)
Assay Temperature: 37° C.
Assay pH: 4.3 (or 7.0, if desired)
Reaction time: 20 min After suspension in water the starch is hydrolyzed by the alpha-amylase, giving soluble blue fragments. The absorbance of the resulting blue solution, measured at 620 nm, is a function of the alpha-amylase activity. One Fungal alpha-Amylase Unit (1 FAU) is the amount of enzyme which breaks down 5.26 g starch (Merck, Amylum soluble Erg. B. 6, Batch 9947275) per hour at the standard assay conditions. A more detailed assay description, APTSMYQI-3207, is available on request from Novozymes A/S, Krogshoejvej 36, DK-2880 Bagsvaerd, Denmark.

Lipase

Substrate: para-Nitro-Phenyl (pNP) Valerate
Assay pH: 7.7
Assay temperature: 40° C.
Reaction time: 25 min The digested product with yellow colour has a characteristic absorbance at 405 nm. Its quantity is determined by spectrophotometry. One lipase unit is the amount of enzyme which releases 1 micromole titratable butyric acid per minute under the given assay conditions. A more detailed assay description, AF95/6-GB, is available on request from Novozymes A/S, Krogshoejvej 36, DK-2880 Bagsvaerd, Denmark.

Protease

Substrate: Suc-AAPF-pNA (Sigma® S-7388).
Assay buffer: 100 mM succinic acid, 100 mM HEPES (Sigma H-3375), 100 mM CHES (Sigma C-2885), 100 mM CABS (Sigma C-5580), 1 mM $CaCl_2$, 150 mM KCl, 0.01% Triton® X-100 adjusted to pH 9.0 with HCl or NaOH.
Assay temperature: 25° C.

300 µl diluted protease sample was mixed with 1.5 ml of the assay buffer and the activity reaction was started by adding 1.5 ml pNA substrate (50 mg dissolved in 1.0 ml DMSO and further diluted 45× with 0.01% Triton® X-100) and, after mixing, the increase in $A_{405}$ was monitored by a spectrophotometer as a measurement of the protease activity. The protease samples were diluted prior to the activity measurement in order to ensure that all activity measurements fell within the linear part of the dose-response curve for the assay.

Example 2

In vivo Screening Test for Amylase Efficacy

The purified *Bacillus* amylases of amino acids 1-486 of SEQ ID NO: 1, amino acids 1-481 of SEQ ID NO: 2 and amino acids 1-483 of SEQ ID NO: 3 were tested in female Göttingen minipigs (Ellegaard), together with a purified fungal amylase derived from *Aspergillus oryzae*, being below 50% identical to any one of SEQ ID NOs: 1-3. Pancreatic Exocrine Insufficiency (PEI) was induced in the minipigs by ligation of the pancreatic duct, and they were also fitted with an ileo-caecal re-entrant cannula, all under halothane anaesthesia and at a weight of about 25 kg, as described in Tabeling et al., J. 1999, Studies on nutrient digestibilities (pre-caecal and total) in pancreatic duct-ligated pigs and the effects of enzyme substitution, J. Anim. Physiol. A. Anim. Nutr. 82: 251-263 (hereinafter referred to as "Tabeling 1999"); and in Gregory et al., J. 1999. Growth and digestion in pancreatic duct ligated pigs, Effect of enzyme supplementation in "Biology of the Pancreas in Growing Animals" (SG Pierzynowski & R. Zabielski eds), Elsevier Science BV, Amsterdam, pp 381-393 (hereinafter referred to as "Gregory et al 1999"). A period of at least 4 weeks was allowed for recovery from surgery, before studies were commenced. Prior to study begin, the PEI status of each pig was confirmed via the stool chymotrypsin test (commercially available from Immundiagnostik AG, Wiesenstrasse 4, D-64625 Bensheim, Germany, with catalogue No. K 6990).

During the studies, the pigs were housed in modified metabolism cages on a 12:12 h light-dark cycle and allowed free access to water and fed two meals/day. The test meal, containing 15.4% protein, 69% starch, and 2.1% fat, had the following composition in g/100 g dry matter: Poultry meat meal 7.1; fishmeal 2.45; casein 4.1; wheat flour 20.65; shelled rice 9.8; potato starch 7.7; maize starch 39.8; cellulose powder 3.0; vitamins 5.3 (as per the nutritional requirements). The pigs were fed 250 g of this test meal mixed with 1 litre water, 0.625 g $Cr_2O_3$ and into which differing amounts of amylases (0, 7500, 18750, 90000 FIP U amylase/meal, see Example 1) were mixed immediately before feeding.

Ileal chyme, collected for a total of 6 h after first appearance of the meal marker in the ileum (green chyme) was frozen at −20° C. immediately after collection, to avoid any bacterial fermentation of the samples. At least one day washout was allowed between separate determinations.

The frozen samples were freeze-dried, milled and analysed for dry matter (DM) and starch. DM was estimated by weight after freeze-drying followed by 8 h incubation at 103° C.; starch was analysed polarimetrically after acid hydrolysis and sugar was estimated gravimetrically. $Cr_2O_3$ was oxidized to chromate and chromium content was calculated via extinction at 365 nm (spectrophotometer), as described by Petry and Rapp in Zeitung für Tierphysiologie (1970), vol. 27, p. 181-189.

Digestibility: Calculation of apparent pre-caecal starch digestibility was made according to the formula, in which $Cr_2O_3$ and starch were expressed as g/100 g dry matter:

$$\text{Apparent digestibility}(\%) = 100 - \left[ \frac{\% \ Cr_2O_3 \ \text{in feed}}{\% \ Cr_2O_3 \ \text{in sample}} \cdot \frac{\% \ \text{starch in sample}}{\% \ \text{starch in feed}} \cdot 100 \right]$$

The apparent starch digestibility results are shown in Table 1 below.

TABLE 1

| Enzyme Supplement | 0 Enzymes | 7500 FIP U | 18750 FIP U | 90000 FIP U |
| --- | --- | --- | --- | --- |
| No supplement | 44.9 +/− 7.6 | | | |
| Pancreatin | | 64.1 +/− 15.2 | 76.7 +/− 13.2 | 97.2 +/− 2.2 |
| Amylase of SEQ ID NO: 1 | | 87.2 +/− 4.3 | 95.4 +/− 1.6 | 96.4 +/− 3.0 |
| Amylase of SEQ ID NO: 3 | | 89.0 +/− 6.8 | 92.5 +/− 3.8 | 96.8 +/− 2.6 |
| Amylase of SEQ ID NO: 2 | | 93.9 +/− 8.4 | 93.4 +/− 6.8 | 96.7 +/− 2.6 |
| *Aspergillus oryzae* amylase | | 49.0 +/− 16.2 | 52.6 +/− 7.5 | 59.9 +/− 12.5 |

Values are mean ± SD

From the results in Table 1 it is apparent that the amylases of the invention perform much better than the known *Aspergillus oryzae* amylase and better than known pancreatin preparations. The amylases of the invention caused a strong and dose dependent improvement on starch digestibility, already showing a highly efficient improvement at the lowest dosage tested.

Example 3

Amylase pH Profiles, with and without Bile Salts

For use in the treatment of PEI and related diseases it is preferable for pancreatic replacement enzymes to have a high activity around pH 6-7 (typical conditions of the upper small intestines). This experiment serves to determine the pH profiles of four alpha-amylases, three bacterial amylases of the invention and a prior art fungal *Aspergillus oryzae* amylase, with and without added bile salts.

Materials and Methods

Enzymes

The amylases used for this study were the purified *Bacillus* amylases of amino acids 1-486 of SEQ ID NO: 1 ("SEQ 1"), amino acids 1-481 of SEQ ID NO: 2 ("SEQ 2") and amino acids 1-483 of SEQ ID NO: 3 ("SEQ 3"), and, for comparison, a purified fungal amylase derived from *Aspergillus oryzae* ("*A. oryzae*"), the amylase of the commercial Fungamyl™ amylase product, which is available from Novozymes A/S, Krogshoejvej 36, DK-2880 Bagsvaerd, Denmark.

pH-profile—Reducing Sugar Assay

Enzyme buffer: 50 mM acetate, 50 mM imidazole, 50 mM malonic acid, 1 mM $CaCl_2$, 0.01% Triton X-100. Adjust to pH 2.0, 3.0, 4.0, 5.0, 6.0, or 7.0 with HCl/NaOH.

Substrate buffer: 1.5 mg/ml amylopectin (waxy corn, e.g. Waxy corn 04201 from Cerestar, batch WM5671), 50 mM acetate, 50 mM imidazole, 50 mM malonic acid, 1 mM $CaCl_2$. Adjust to the desired pH (as above) with HCl/NaOH. Incubate for 5 min at 100° C. The substrate buffer was made with or without 5 mM bile salts (i.e. Sodium taurocholate BRP, lot 2, from the Ph. Eur or FIP, also commercially available from e.g. LGC promochem, 500 g/mol).

The amylase activity was detected by reducing sugar assay. Briefly, 50 µl enzyme (diluted in enzyme buffer so as to fall within the linear range of the assay) was mixed with 100 µl substrate buffer in PCR-MTP (Thermo-Fast® 96, ABgene, cat. no. AB-0600). The MTP's were incubated at 37° C. for 15 min, following which 75 µl stop solution (100 mM p-hydroxybenzoic acid hydrazide, 180 mM K-Na-tartrate, 2% NaOH) was added, and the plates were incubated at 95° C. for 10 min. Then 150 µl from each well was transferred to 96-well MTP, and the absorbance at 410 nm was monitored as a measure of amylase activity.

Results

The results (average of duplicate determinations) are shown in Tables 2-4, below.

Table 2 shows the activity of each enzyme at the pH indicated in the absence of bile salts. For each enzyme, the maximum activity was set to 100%.

Table 3 shows the same as Table 2, but in the presence of 5 mM bile salts.

Table 4 shows the activity of each enzyme per mg enzyme protein at the pH indicated in the absence of bile salts, relative to the maximum enzyme activity measured in this experiment, which was the activity of the SEQ 1 enzyme at pH 5.0 (100%). The activity of each enzyme has accordingly been normalized relative to this activity. The amount of enzyme protein for each enzyme was determined on the basis of the specific activity.

Table 5 shows the same as Table 4, but in the presence of 5 mM bile salts. Here the activity of the SEQ 1 enzyme at pH 5.0 in the presence of 5 mM bile salts is the reference value (100%).

TABLE 2

| Relative activity without bile salts | | | | | | |
|---|---|---|---|---|---|---|
| Enzyme/pH | 2 | 3 | 4 | 5 | 6 | 7 |
| A.oryzae | 0.0 | 0.0 | 77.4 | 93.4 | 100.0 | 25.6 |
| SEQ 2 | 0.4 | 0.2 | 7.8 | 51.8 | 100.0 | 76.1 |
| SEQ 3 | 0.3 | 0.8 | 2.8 | 22.2 | 79.7 | 100.0 |
| SEQ 1 | 0.1 | 1.8 | 29.4 | 100.0 | 86.0 | 71.1 |

TABLE 3

| Relative activity with bile salts | | | | | | |
|---|---|---|---|---|---|---|
| Enzyme/pH | 2 | 3 | 4 | 5 | 6 | 7 |
| A.oryzae | 0.0 | 0.0 | 53.5 | 71.8 | 68.6 | 16.1 |
| SEQ 2 | 0.1 | 0.0 | 0.5 | 37.5 | 85.8 | 66.1 |
| SEQ 3 | 0.0 | 0.0 | 0.8 | 2.5 | 61.4 | 78.1 |
| SEQ 1 | 0.0 | 0.0 | 10.4* | 76.0 | 68.6 | 59.7 |

*One measurement discarded for being clearly erroneous

TABLE 4

| Normalized absolute activities relative to SEQ. 1 without bile salts | | | | | | |
|---|---|---|---|---|---|---|
| Enzyme/pH | 2 | 3 | 4 | 5 | 6 | 7 |
| A.oryzae | 0.0 | 0.0 | 10.9 | 13.2 | 14.1 | 3.6 |
| SEQ 2 | 0.1 | 0.1 | 2.1 | 14.0 | 27.1 | 20.6 |
| SEQ 3 | 0.1 | 0.4 | 1.4 | 10.7 | 38.3 | 48.0 |
| SEQ 1 | 0.1 | 1.8 | 29.4 | 100.0 | 86.0 | 71.1 |

TABLE 5

| Normalized absolute activities relative to SEQ 1, with bile salts | | | | | | |
|---|---|---|---|---|---|---|
| Enzyme/pH | 2 | 3 | 4 | 5 | 6 | 7 |
| A. oryzae | 0.0 | 0.0 | 9.9 | 13.3 | 12.7 | 3.0 |
| SEQ 2 | 0.0 | 0.0 | 0.2 | 13.4 | 30.6 | 23.6 |
| SEQ 3 | 0.0 | 0.0 | 0.5 | 1.6 | 38.8 | 49.3 |
| SEQ 1 | 0.0 | 0.0 | 13.7 | 100.0 | 90.2 | 78.6 |

These results show that although bile salts seem to slightly reduce the amylase activity, the activity in the presence of 5 mM bile salts is still satisfactory. The results also show that bile salts do not lead to a shift of the pH optimum.

The results furthermore show that each of the *Bacillus* amylases of the invention all have more than 50% relative activity at pH 7, which is not the case for the comparative fungal amylase.

Finally, Tables 4 and 5 demonstrate that, at least under these conditions, the amylase having amino acids 1-486 of SEQ ID NO: 1 has a significantly higher activity per mg enzyme than all the other amylases tested.

Example 4

Amylase Degradation Profile

The degradation profile (DP1-10 qualitative fingerprint) of five alpha-amylases was determined by degradation of waxy maize starch followed by analysis on HPLC.

Materials and Methods

The enzymes were purified Bacillus amylases of amino acids 1-486 of SEQ ID NO: 1 ("SEQ 1"), amino acids 1-481 of SEQ ID NO: 2 ("SEQ 2") and amino acids 1-483 of SEQ ID NO: 3 ("SEQ 3"), and, for comparison, a purified fungal amylase derived from *Aspergillus oryzae* ("*A. oryzae*"), the amylase of the commercial Fungamyl™ amylase product, which is available from Novozymes A/S, Krogshoejvej 36, DK-2880 Bagsvaerd, Denmark. Pancreatin was from Solvay Pharmaceuticals.

As substrate a slurry of 50 mg/mL waxy maize starch (e.g. Waxy corn 04201 from Cerestar, Batch: WM5671) was made in 50 mM Na-acetate buffer pH 6.0, 40 ppm $Ca^{2+}$.

Purified enzymes were dosed at a concentration of 0.0073 mg enzyme protein per g of dry substance of the reaction mixture. The amount of amylase enzyme protein was calculated on the basis of the $A_{280}$ values and the amino acid sequences (amino acid compositions) using the principles outlined in S. C. Gill & P. H. von Hippel, Analytical Biochemistry 182, 319-326, (1989). After dosing the enzyme, the reaction was incubated at 60° C. Aliquots were withdrawn after 24 hours and diluted 1:1 in demineralized water and two drops of 1 M HCl was added. The enzymes were inactivated by boiling for 15 min. The samples were filtered through a 0.2 µm filter prior to application on the HPLC fitted with two Aminex HPX 42A (Biorad) columns connected in series and using water as eluent.

100 mg of pancreatin was dissolved in 10 mL 50 mM Na-acetate buffer pH 5.5. 20 ul of this solution was added to 1 mL substrate slurry (50 mg/mL waxy corn starch in 50 mM Na-acetate pH 5.5) and incubated at 37° C. for 24 hours, and then inactivated and filtered as described above prior to application on the HPLC.

In a separate experiment (not shown), the "SEQ 1" amylase was also tested at 37° C. which gave rise to the same degradation profile as at 60° C.

Results

Figure 2:
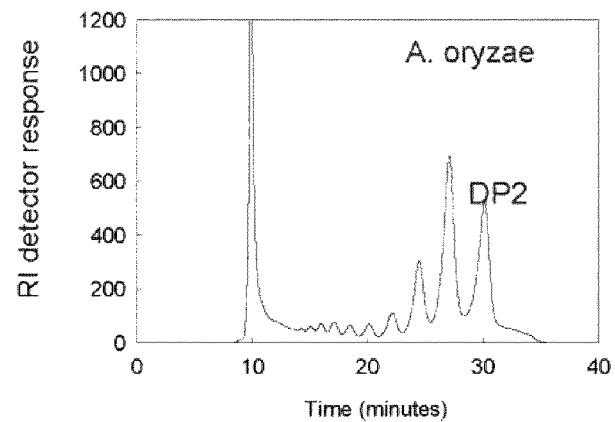
FIG. 2 shows a chromatogram representing the degradation profile of an amylase from *Aspergillus oryzae*.
Figure 3:
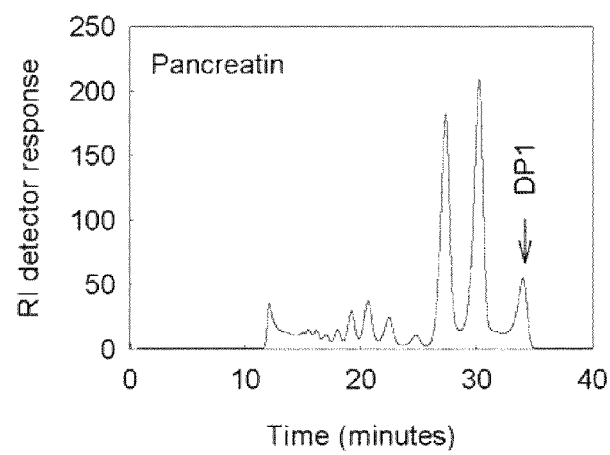
FIG. 3 shows a chromatogram representing the degradation profile of Pancreatin.
Figure 4:
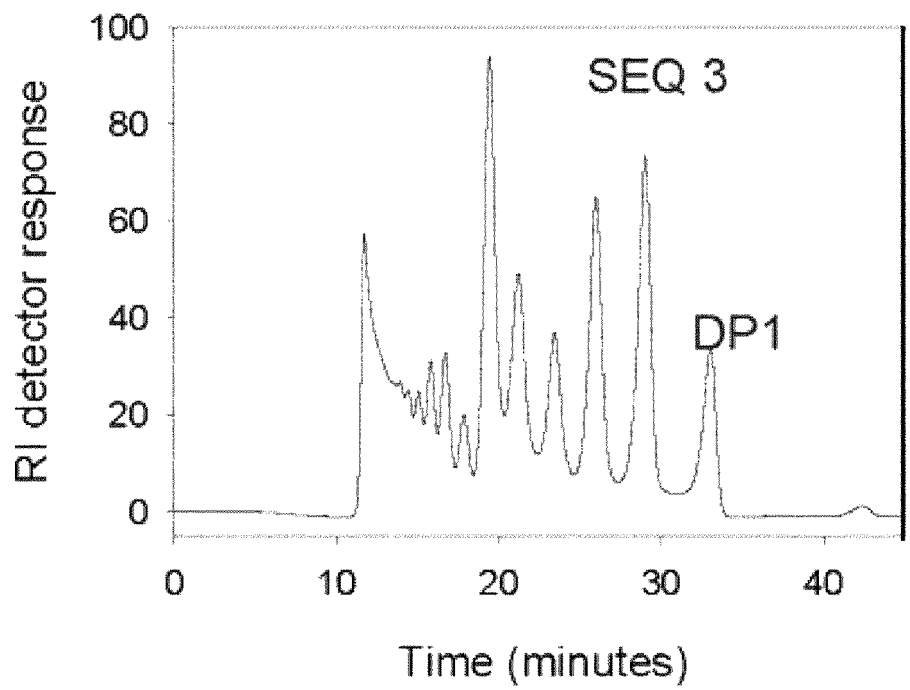
FIG. 4 shows a chromatogram representing the degradation profile of an amylase having the amino acid sequence of amino acids 1-483 of SEQ ID NO: 3 (a *Bacillus* sp. amylase variant)
Figure 5:
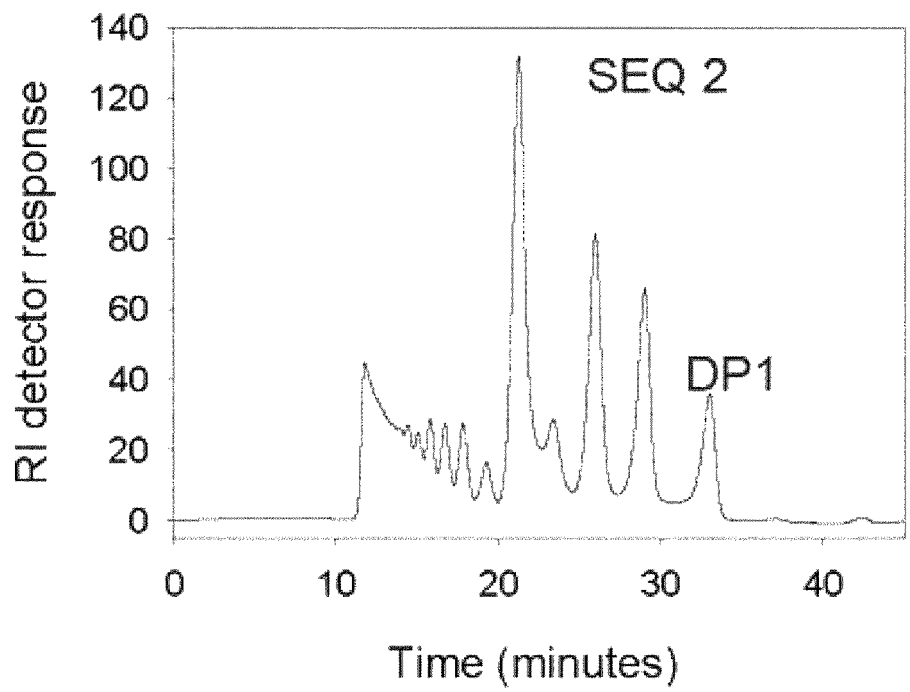
FIG. 5 shows a chromatogram representing the degradation profile of an amylase having the amino acid sequence of amino acids 1-481 of SEQ ID NO: 2 (a *Bacillus licheniformis* amylase variant).

The resulting chromatograms after 24 hours of incubation are shown in FIGS. 1-5 together with indications as to which compound is represented by which peak in the chromatogram. For the sake of clarity, these indications have been inserted in FIG. 1 only, but they apply mutatis mutandis to each of the other figures as well. The designation DP stands for Degree of Polymerization. Thus, DP1 designates the monomer, DP2 the dimer, DP3 the trimer, DP4 the tetramer, DP5 the pentamer, DP6 the hexamer, and so forth.

It appears from the figures, that the fungal alpha-amylase ("*A. oryzae*") generates DP2, DP3 and DP4 as the main degradation products, whereas it leaves a large fraction non-hydrolysed (large peak at retention time 10 minutes). DP1 was not detected as a degradation product.

The bacterial alpha-amylases on the other hand ("SEQ 1", "SEQ 2", "SEQ 3") in general produce DP1, DP2, DP3 and either of DP5 or DP6 as main products, leaving only a small part of non-hydrolysed substrate. Generally, a low amount of DP4 appears to be produced.

As far as Pancreatin is concerned, it appears to behave like a mixture of the fungal and bacterial amylases described above, i.e. generating small DP products (DP1, DP2 and DP3), almost nothing of DP4, DP5 and DP6, and only leaving a small non-hydrolysed substrate peak.

Example 5

Pharmaceutical Amylase Compositions (A) High-strength Pellets

A liquid concentrate was prepared as described in DK 2005 00931 (a germ-filtered ultrafiltrate) of the amylase having amino acids 1-486 of SEQ ID NO: 1. The liquid concentrate was spray-dried. The measured amylase protein content of the spray-dried amylase powder was 37%. 1125 g of the spray-dried amylase powder was dry pre-mixed together with microcrystalline cellulose (450 g) and polyethylene glycol 4000 (Macrogol™ 4000; 675 g) in a commercially available mixer. Isopropyl alcohol 100% (460 g) was added and the resulting wet mass was continued to be thoroughly mixed at room temperature. The homogenized mass was then extruded in a commercially available extruder which was fitted with a piercing die having a hole diameter of 0.8 mm to form cylindrical pellets. The bead temperature was not exceeding 50° C. while extruding. The extrudate produced was rounded to spherical pellets with a commercially available spheronizer by adding the necessary amount of isopropyl alcohol 100% (75.5 g). The pellets were dried at a supply temperature of approximately 40° C. in a commercially available vacuum dryer (from Voetsch). The product temperature did not exceed 45° C. The dried pellets were then separated by using a mechanical sieving machine with 0.7 and 1.4 mm screens. The sieve fractions of ≧0.7 mm and ≦1.4 mm were collected and can be filled in portions of 200 mg pellets each in capsules of size 2. The amylase concentration of the resulting dry pellets was approximately 18.5% (w/w).

(B) Lower-strength Pellets

Similar to the example provided above (A), pellets with a lower content of amylase were produced using 562.5 g of the same spray-dried amylase powder, microcrystalline cellulose (1125 g), polyethylene glycol 4000 (562.5 g), isopropyl alcohol for moistening (700 g) and isopropyl alcohol for rounding (41.6 g). The amylase concentration of the resulting dry pellets was approximately 9.3% (w/w).

The resulting pellets from examples (A) and (B) were tested for amylolytic activity by applying a modified FIP method for microbial amylases. In principle, starch is hydrolysed by amylase at pH 5.8 and at a constant temperature (37.0+/−0.1° C.) in the presence of sodium chloride and calcium chloride. The reducing groups resulting from the hydrolysis react with iodine in alkaline solution and the excess of iodine was titrated with thiosulphate. One unit of amylase is defined as the amount of enzyme, which, under the defined conditions and substrate, hydrolyzes 1 micromol of glycosidic bond per minute. The amylolytic activity in the pellets was found to be approximately 96% relative to the amylolytic activity in the starting powdery amylase material for each of the examples (A) and (B).

The resulting pellets from examples (A) and (B) were then tested for disintegration according to Pharm. Eur. 2.9.1. (Section "Disintegration of tablets and capsules") (test solution: water—500 mL, 37° C.). The disintegration of the pellets from example (A) was completed within 15 min. The disintegration of the pellets from example (B) was completed within 9 min.

Example 6

Pharmaceutical Compositions of Amylase and Protease

High-strength pellets containing amylase and protease were prepared as follows:

A germ-filtered liquid concentrate of the protease of amino acids 1-274 of SEQ ID NO: 5 was prepared as described in Example 1 of DK patent application no. 2005 00930 and spray-dried. Spray-dried amylase in powder form (398.5 g) prepared as described in Example 5 was dry pre-mixed together with the spray-dried protease powder (746.5 g, having a measured protease protein content of 58.5%), microcrystalline cellulose (458 g) and polyethylene glycol 4000 (Macrogol™ 4000; 687 g) in a commercially available mixer. Isopropyl alcohol 100% (460 g) was added and the resulting wet mass was continued to be thoroughly mixed at room temperature. The homogenized mass was then extruded in a commercially available extruder which was fitted with a piercing die having a hole diameter of 0.8 mm to form cylindrical pellets. The bead temperature was not exceeding 50° C. while extruding. The extrudate produced was rounded to spherical pellets with a commercially available spheronizer by adding the necessary amount of isopropyl alcohol 100% (58 g). The pellets were dried using a supply temperature of approximately 40° C. in a commercially available vacuum dryer (from Voetsch). The product temperature did not exceed 45° C. The dried pellets were then separated by using a mechanical sieving machine with 0.7 and 1.4 mm screens. The sieve fractions of ≧0.7 mm and ≦1.4 mm were collected and can be filled in portions of 200 mg each in capsules of size 2.

The resulting pellets from were tested for proteolytic and amylolytic activities according to the methods as outlined above. No loss in proteolytic or amylolytic activity was found in the pellets in each case relative to the starting powdery protease or amylase material, respectively.

The invention claimed is:

1. A method for the treatment of digestive disorders, pancreatic exocrine insufficiency, pancreatitis, cystic fibrosis, diabetes type I, and/or diabetes type II, by administering an effective amount of an amylase having at least 95% identity to (i) amino acids 1-481 of SEQ ID NO: 1, (ii) amino acids 1-481 of SEQ ID NO: 2, and/or (iii) amino acids 1-483 of SEQ ID NO: 3 to an animal in need thereof.

2. The method of claim 1, further comprising administering an effective amount of a lipase or a protease to the animal.

3. The method of claim 1, further comprising administering an effective amount of a lipase and a protease to the animal.

4. The method of claim 2, wherein the protease has at least 95% identity to a protease selected from the group consisting of:
   (a) a protease having amino acids 1-274 of SEQ ID NO: 5,
   (b) a protease having amino acids 1-188 of SEQ ID NO: 6, and
   (c) a protease having amino acids 1-188 of SEQ ID NO: 7.

5. The method of claim 2, wherein the protease is selected from the group consisting of:
   a) a protease comprising amino acids 1-274 of SEQ ID NO: 5,
   b) a protease comprising amino acids 1-188 of SEQ ID NO: 6, and
   c) a protease comprising amino acids 1-188 of SEQ ID NO: 7.

6. The method of claim 1, wherein the amylase has an amino acid sequence selected from the group consisting of (i) amino acids 1-481, 1-484, 1-486, or 1-513 of SEQ ID NO: 1, (ii) amino acids 1-481 of SEQ ID NO: 2, and/or (iii) amino acids 1-483 of SEQ ID NO: 3.

7. The method of claim 1, wherein the amylase has an amino acid sequence consisting of amino acids 1-481, 1-484, 1-486, or 1-513 of SEQ ID NO: 1.

8. The method of claim 1, wherein the amylase has an amino acid sequence consisting of amino acids 1-481 of SEQ ID NO: 2.

9. The method of claim 1, wherein the amylase has an amino acid sequence consisting of amino acids amino acids 1-483 of SEQ ID NO: 3.

10. A method of treating pancreatic exocrine insufficiency comprising administering an effective amount of an amylase having at least 95% identity to (i) amino acids 1-481 of SEQ ID NO: 1, (ii) amino acids 1-481 of SEQ ID NO: 2, and/or (iii) amino acids 1-483 of SEQ ID NO: 3 to an animal in need thereof.

11. The method of claim 10, wherein the amylase has an amino acid sequence selected from the group consisting of (i) amino acids 1-481, 1-484, 1-486, or 1-513 of SEQ ID NO: 1, (ii) amino acids 1-481 of SEQ ID NO: 2, and/or (iii) amino acids 1-483 of SEQ ID NO: 3.

12. The method of claim 10, wherein the amylase has an amino acid sequence consisting of amino acids 1-481, 1-484, 1-486, or 1-513 of SEQ ID NO: 1.

13. The method of claim 10, wherein the amylase has an amino acid sequence consisting of amino acids 1-481 of SEQ ID NO: 2.

14. The method of claim 10, wherein the amylase has an amino acid sequence consisting of amino acids amino acids 1-483 of SEQ ID NO: 3.

15. The method of claim 10, further comprising administering an effective amount of a lipase or a protease.

16. The method of claim 15, wherein the protease has at least 95% identity to a protease selected from the group consisting of:
   (a) a protease having amino acids 1-274 of SEQ ID NO: 5,
   (b) a protease having amino acids 1-188 of SEQ ID NO: 6, and
   (c) a protease having amino acids 1-188 of SEQ ID NO: 7.

17. The method of claim 15, wherein the protease is selected from the group consisting of:
   a) a protease comprising amino acids 1-274 of SEQ ID NO: 5,
   b) a protease comprising amino acids 1-188 of SEQ ID NO: 6, and
   c) a protease comprising amino acids 1-188 of SEQ ID NO: 7.

18. The method of claim 1, wherein the animal is human.

19. The method of claim 10, wherein the animal is human.

20. The method of claim 10, further comprising administering an effective amount of a lipase and a protease to the animal.

* * * * *

SEQUENCE LISTING

<160> NUMBER OF SEQ ID NOS: 16

<210> SEQ ID NO 1
<211> LENGTH: 513
<212> TYPE: PRT
<213> ORGANISM: Bacillus stearothermophilus
<220> FEATURE:
<221> NAME/KEY: VARIANT
<222> LOCATION: (1)..(513)

<400> SEQUENCE: 1

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Lys Ala Trp Asp Trp Glu Val Asp Thr Glu Phe Gly
            180                 185                 190

Asn Tyr Asp Tyr Leu Met Tyr Ala Asp Leu Asp Met Asp His Pro Glu
        195                 200                 205

Val Val Thr Glu Leu Lys Asn Trp Gly Lys Trp Tyr Val Asn Thr Thr
    210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
                245                 250                 255

Leu Phe Thr Val Gly Glu Tyr Trp Ser Tyr Asp Ile Asn Lys Leu His
            260                 265                 270

Asn Tyr Ile Thr Lys Thr Asp Gly Thr Met Ser Leu Phe Asp Ala Pro
        275                 280                 285

Leu His Asn Lys Phe Tyr Thr Ala Ser Lys Ser Gly Gly Ala Phe Asp
    290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
            340                 345                 350
```

```
Leu Thr Arg Gln Glu Gly Tyr Pro Cys Val Phe Tyr Gly Asp Tyr Tyr
            355                 360                 365

Gly Ile Pro Gln Tyr Asn Ile Pro Ser Leu Lys Ser Lys Ile Asp Pro
        370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
                405                 410                 415

Lys Pro Gly Ser Gly Leu Ala Ala Leu Ile Thr Asp Gly Pro Gly Gly
            420                 425                 430

Ser Lys Trp Met Tyr Val Gly Lys Gln His Ala Gly Lys Val Phe Tyr
                435                 440                 445

Asp Leu Thr Gly Asn Arg Ser Asp Thr Val Thr Ile Asn Ser Asp Gly
        450                 455                 460

Trp Gly Glu Phe Lys Val Asn Gly Gly Ser Val Ser Val Trp Val Pro
465                 470                 475                 480

Arg Lys Thr Thr Val Ser Thr Ile Ala Arg Pro Ile Thr Thr Arg Pro
                485                 490                 495

Trp Thr Gly Glu Phe Val Arg Trp Thr Glu Pro Arg Leu Val Ala Trp
            500                 505                 510

Pro

<210> SEQ ID NO 2
<211> LENGTH: 481
<212> TYPE: PRT
<213> ORGANISM: Bacillus licheniformis
<220> FEATURE:
<221> NAME/KEY: VARIANT
<222> LOCATION: (1)..(481)

<400> SEQUENCE: 2

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Thr Ser
        35                  40                  45

Gln Ala Asp Val Gly Tyr Gly Ala Tyr Asp Leu Tyr Asp Leu Gly Glu
    50                  55                  60

Phe His Gln Lys Gly Thr Val Arg Thr Lys Tyr Gly Thr Lys Gly Glu
65                  70                  75                  80

Leu Gln Ser Ala Ile Lys Ser Leu His Ser Arg Asp Ile Asn Val Tyr
                85                  90                  95

Gly Asp Val Val Ile Asn His Lys Gly Gly Ala Asp Ala Thr Glu Asp
            100                 105                 110

Val Thr Ala Val Glu Val Asp Pro Ala Asp Arg Asn Arg Val Ile Ser
        115                 120                 125

Gly Glu His Leu Ile Lys Ala Trp Thr His Phe His Phe Pro Gly Arg
    130                 135                 140

Gly Ser Thr Tyr Ser Asp Phe Lys Trp Tyr Trp Tyr His Phe Asp Gly
145                 150                 155                 160

Thr Asp Trp Asp Glu Ser Arg Lys Leu Asn Arg Ile Tyr Lys Phe Gln
                165                 170                 175

Gly Lys Thr Trp Asp Trp Glu Val Ser Asn Glu Phe Gly Asn Tyr Asp
            180                 185                 190
```

```
Tyr Leu Met Tyr Ala Asp Ile Asp Tyr Asp His Pro Asp Val Val Ala
            195                 200                 205

Glu Ile Lys Arg Trp Gly Thr Trp Tyr Ala Asn Glu Leu Gln Leu Asp
210                 215                 220

Gly Phe Arg Leu Asp Ala Val Lys His Ile Lys Phe Ser Phe Leu Arg
225                 230                 235                 240

Asp Trp Val Asn His Val Arg Glu Lys Thr Gly Lys Glu Met Phe Thr
                245                 250                 255

Val Ala Glu Tyr Trp Ser Asn Asp Leu Gly Ala Leu Glu Asn Tyr Leu
            260                 265                 270

Asn Lys Thr Asn Phe Asn His Ser Val Phe Asp Val Pro Leu His Tyr
        275                 280                 285

Gln Phe His Ala Ala Ser Thr Gln Gly Gly Gly Tyr Asp Met Arg Lys
    290                 295                 300

Leu Leu Asn Gly Thr Val Val Ser Lys His Pro Leu Lys Ser Val Thr
305                 310                 315                 320

Phe Val Asp Asn His Asp Thr Gln Pro Gly Gln Ser Leu Glu Ser Thr
                325                 330                 335

Val Gln Thr Trp Phe Lys Pro Leu Ala Tyr Ala Phe Ile Leu Thr Arg
            340                 345                 350

Glu Ser Gly Tyr Pro Gln Val Phe Tyr Gly Asp Met Tyr Gly Thr Lys
        355                 360                 365

Gly Asp Ser Gln Arg Glu Ile Pro Ala Leu Lys His Lys Ile Glu Pro
    370                 375                 380

Ile Leu Lys Ala Arg Lys Gln Tyr Ala Tyr Gly Ala Gln His Asp Tyr
385                 390                 395                 400

Phe Asp His His Asp Ile Val Gly Trp Thr Arg Glu Gly Asp Ser Ser
                405                 410                 415

Val Ala Asn Ser Gly Leu Ala Ala Leu Ile Thr Asp Gly Pro Gly Gly
            420                 425                 430

Ala Lys Arg Met Tyr Val Gly Arg Gln Asn Ala Gly Glu Thr Trp His
        435                 440                 445

Asp Ile Thr Gly Asn Arg Ser Glu Pro Val Val Ile Asn Ser Glu Gly
    450                 455                 460

Trp Gly Glu Phe His Val Asn Gly Gly Ser Val Ser Ile Tyr Val Gln
465                 470                 475                 480

Arg

<210> SEQ ID NO 3
<211> LENGTH: 483
<212> TYPE: PRT
<213> ORGANISM: Bacillus sp.
<220> FEATURE:
<221> NAME/KEY: VARIANT
<222> LOCATION: (1)..(483)

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
```

```
            65                  70                  75                  80
Thr Arg Asn Gln Leu Gln Ala Ala Val Asn Ala Leu Lys Ser Asn Gly
                85                  90                  95
Ile Gln Val Tyr Gly Asp Val Val Met Asn His Lys Gly Gly Ala Asp
                100                 105                 110
Ala Thr Glu Met Val Lys Ala Val Glu Val Asn Pro Asn Asn Arg Asn
                115                 120                 125
Gln Glu Val Ser Gly Glu Tyr Thr Ile Glu Ala Trp Thr Lys Phe Asp
        130                 135                 140
Phe Pro Gly Arg Gly Asn Thr His Ser Asn Phe Lys Trp Arg Trp Tyr
145                 150                 155                 160
His Phe Asp Gly Val Asp Trp Asp Gln Ser Arg Lys Leu Asn Asn Arg
                165                 170                 175
Ile Tyr Lys Phe Arg Gly Lys Gly Trp Asp Trp Glu Val Asp Thr Glu
                180                 185                 190
Phe Gly Asn Tyr Asp Tyr Leu Met Tyr Ala Asp Ile Asp Met Asp His
                195                 200                 205
Pro Glu Val Val Asn Glu Leu Arg Asn Trp Gly Val Trp Tyr Thr Asn
        210                 215                 220
Thr Leu Gly Leu Asp Gly Phe Arg Ile Asp Ala Val Lys His Ile Lys
225                 230                 235                 240
Tyr Ser Phe Thr Arg Asp Trp Ile Asn His Val Arg Ser Ala Thr Gly
                245                 250                 255
Lys Asn Met Phe Ala Val Ala Glu Phe Trp Lys Asn Asp Leu Gly Ala
                260                 265                 270
Ile Glu Asn Tyr Leu Asn Lys Thr Asn Trp Asn His Ser Val Phe Asp
                275                 280                 285
Val Pro Leu His Tyr Asn Leu Tyr Asn Ala Ser Lys Ser Gly Gly Asn
        290                 295                 300
Tyr Asp Met Arg Gln Ile Phe Asn Gly Thr Val Val Gln Lys His Pro
305                 310                 315                 320
Met His Ala Val Thr Phe Val Asp Asn His Asp Ser Gln Pro Glu Glu
                325                 330                 335
Ala Leu Glu Ser Phe Val Glu Glu Trp Phe Lys Pro Leu Ala Tyr Ala
                340                 345                 350
Leu Thr Leu Thr Arg Glu Gln Gly Tyr Pro Ser Val Phe Tyr Gly Asp
                355                 360                 365
Tyr Tyr Gly Ile Pro Thr His Gly Val Pro Ala Met Lys Ser Lys Ile
        370                 375                 380
Asp Pro Ile Leu Glu Ala Arg Gln Lys Tyr Ala Tyr Gly Arg Gln Asn
385                 390                 395                 400
Asp Tyr Leu Asp His His Asn Ile Ile Gly Trp Thr Arg Glu Gly Asn
                405                 410                 415
Thr Ala His Pro Asn Ser Gly Leu Ala Thr Ile Met Ser Asp Gly Ala
                420                 425                 430
Gly Gly Asn Lys Trp Met Phe Val Gly Arg Asn Lys Ala Gly Gln Val
                435                 440                 445
Trp Thr Asp Ile Thr Gly Asn Lys Ala Gly Thr Val Thr Ile Asn Ala
        450                 455                 460
Asp Gly Trp Gly Asn Phe Ser Val Asn Gly Gly Ser Val Ser Ile Trp
465                 470                 475                 480

Val Asn Lys
```

```
<210> SEQ ID NO 4
<211> LENGTH: 485
<212> TYPE: PRT
<213> ORGANISM: Bacillus halmapalus
<220> FEATURE:
<221> NAME/KEY: mat_peptide
<222> LOCATION: (1)..(485)

<400> SEQUENCE: 4
```

| His | His | Asn | Gly | Thr | Asn | Gly | Thr | Met | Met | Gln | Tyr | Phe | Glu | Trp | His |
|---|---|---|---|---|---|---|---|---|---|---|---|---|---|---|---|
| 1 | | | | 5 | | | | | 10 | | | | | 15 | |

| Leu | Pro | Asn | Asp | Gly | Asn | His | Trp | Asn | Arg | Leu | Arg | Asp | Asp | Ala | Ser |
| | | | 20 | | | | | 25 | | | | | 30 | | |

| Asn | Leu | Arg | Asn | Arg | Gly | Ile | Thr | Ala | Ile | Trp | Ile | Pro | Pro | Ala | Trp |
| | | 35 | | | | | 40 | | | | | 45 | | | |

| Lys | Gly | Thr | Ser | Gln | Asn | Asp | Val | Gly | Tyr | Gly | Ala | Tyr | Asp | Leu | Tyr |
| | 50 | | | | | 55 | | | | | 60 | | | | |

| Asp | Leu | Gly | Glu | Phe | Asn | Gln | Lys | Gly | Thr | Val | Arg | Thr | Lys | Tyr | Gly |
| 65 | | | | | 70 | | | | | 75 | | | | | 80 |

| Thr | Arg | Ser | Gln | Leu | Glu | Ser | Ala | Ile | His | Ala | Leu | Lys | Asn | Asn | Gly |
| | | | | 85 | | | | | 90 | | | | | 95 | |

| Val | Gln | Val | Tyr | Gly | Asp | Val | Val | Met | Asn | His | Lys | Gly | Gly | Ala | Asp |
| | | | 100 | | | | | 105 | | | | | 110 | | |

| Ala | Thr | Glu | Asn | Val | Leu | Ala | Val | Glu | Val | Asn | Pro | Asn | Asn | Arg | Asn |
| | | 115 | | | | | 120 | | | | | 125 | | | |

| Gln | Glu | Ile | Ser | Gly | Asp | Tyr | Thr | Ile | Glu | Ala | Trp | Thr | Lys | Phe | Asp |
| | 130 | | | | | 135 | | | | | 140 | | | | |

| Phe | Pro | Gly | Arg | Gly | Asn | Thr | Tyr | Ser | Asp | Phe | Lys | Trp | Arg | Trp | Tyr |
| 145 | | | | | 150 | | | | | 155 | | | | | 160 |

| His | Phe | Asp | Gly | Val | Asp | Trp | Asp | Gln | Ser | Arg | Gln | Phe | Gln | Asn | Arg |
| | | | | 165 | | | | | 170 | | | | | 175 | |

| Ile | Tyr | Lys | Phe | Arg | Gly | Asp | Gly | Lys | Ala | Trp | Asp | Trp | Glu | Val | Asp |
| | | | 180 | | | | | 185 | | | | | 190 | | |

| Ser | Glu | Asn | Gly | Asn | Tyr | Asp | Tyr | Leu | Met | Tyr | Ala | Asp | Val | Asp | Met |
| | | 195 | | | | | 200 | | | | | 205 | | | |

| Asp | His | Pro | Glu | Val | Val | Asn | Glu | Leu | Arg | Arg | Trp | Gly | Glu | Trp | Tyr |
| | 210 | | | | | 215 | | | | | 220 | | | | |

| Thr | Asn | Thr | Leu | Asn | Leu | Asp | Gly | Phe | Arg | Ile | Asp | Ala | Val | Lys | His |
| 225 | | | | | 230 | | | | | 235 | | | | | 240 |

| Ile | Lys | Tyr | Ser | Phe | Thr | Arg | Asp | Trp | Leu | Thr | His | Val | Arg | Asn | Ala |
| | | | | 245 | | | | | 250 | | | | | 255 | |

| Thr | Gly | Lys | Glu | Met | Phe | Ala | Val | Ala | Glu | Phe | Trp | Lys | Asn | Asp | Leu |
| | | | 260 | | | | | 265 | | | | | 270 | | |

| Gly | Ala | Leu | Glu | Asn | Tyr | Leu | Asn | Lys | Thr | Asn | Trp | Asn | His | Ser | Val |
| | | 275 | | | | | 280 | | | | | 285 | | | |

| Phe | Asp | Val | Pro | Leu | His | Tyr | Asn | Leu | Tyr | Asn | Ala | Ser | Asn | Ser | Gly |
| | 290 | | | | | 295 | | | | | 300 | | | | |

| Gly | Asn | Tyr | Asp | Met | Ala | Lys | Leu | Leu | Asn | Gly | Thr | Val | Val | Gln | Lys |
| 305 | | | | | 310 | | | | | 315 | | | | | 320 |

| His | Pro | Met | His | Ala | Val | Thr | Phe | Val | Asp | Asn | His | Asp | Ser | Gln | Pro |
| | | | | 325 | | | | | 330 | | | | | 335 | |

| Gly | Glu | Ser | Leu | Glu | Ser | Phe | Val | Gln | Glu | Trp | Phe | Lys | Pro | Leu | Ala |
| | | | 340 | | | | | 345 | | | | | 350 | | |

| Tyr | Ala | Leu | Ile | Leu | Thr | Arg | Glu | Gln | Gly | Tyr | Pro | Ser | Val | Phe | Tyr |
| | | 355 | | | | | 360 | | | | | 365 | | | |

| Gly | Asp | Tyr | Tyr | Gly | Ile | Pro | Thr | His | Ser | Val | Pro | Ala | Met | Lys | Ala |

```
                          370                 375                 380
Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
                420                 425                 430

Gly Pro Gly Gly Glu Lys Trp Met Tyr Val Gly Gln Asn Lys Ala Gly
                435                 440                 445

Gln Val Trp His Asp Ile Thr Gly Asn Lys Pro Gly Thr Val Thr Ile
            450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 5
<211> LENGTH: 274
<212> TYPE: PRT
<213> ORGANISM: Bacillus licheniformis
<220> FEATURE:
<221> NAME/KEY: mat_peptide
<222> LOCATION: (1)..(274)

<400> SEQUENCE: 5

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
                20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
```

```
                      245                 250                 255
Gly Ser Ser Phe Tyr Tyr Gly Lys Gly Leu Ile Asn Val Glu Ala Ala
                260                 265                 270

Ala Gln

<210> SEQ ID NO 6
<211> LENGTH: 188
<212> TYPE: PRT
<213> ORGANISM: Nocardiopsis sp.
<220> FEATURE:
<221> NAME/KEY: mat_peptide
<222> LOCATION: (1)..(188)

<400> SEQUENCE: 6

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
                20                  25                  30

Ala Gly His Cys Gly Arg Val Gly Thr Gln Val Thr Ile Gly Asn Gly
            35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185

<210> SEQ ID NO 7
<211> LENGTH: 188
<212> TYPE: PRT
<213> ORGANISM: Nocardiopsis dassonvillei subsp. dassonvillei
<220> FEATURE:
<221> NAME/KEY: mat_peptide
<222> LOCATION: (1)..(188)

<400> SEQUENCE: 7

Ala Asp Ile Ile Gly Gly Leu Ala Tyr Tyr Met Gly Gly Arg Cys Ser
1               5                   10                  15

Val Gly Phe Ala Ala Thr Asn Ser Ala Gly Gln Pro Gly Phe Val Thr
                20                  25                  30

Ala Gly His Cys Gly Thr Val Gly Thr Gly Val Thr Ile Gly Asn Gly
            35                  40                  45

Thr Gly Thr Phe Gln Asn Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80
```

-continued

```
Asn Ser Gly Gly Tyr Gln Ser Val Thr Gly Thr Ser Gln Ala Pro Ala
                 85                  90                  95

Gly Ser Ala Val Cys Arg Ser Gly Ser Thr Thr Gly Trp His Cys Gly
            100                 105                 110

Thr Ile Gln Ala Arg Asn Gln Thr Val Arg Tyr Pro Gln Gly Thr Val
        115                 120                 125

Tyr Ser Leu Thr Arg Thr Asn Val Cys Ala Glu Pro Gly Asp Ser Gly
    130                 135                 140

Gly Ser Phe Ile Ser Gly Ser Gln Ala Gln Gly Val Thr Ser Gly Gly
145                 150                 155                 160

Ser Gly Asn Cys Ser Val Gly Thr Thr Tyr Tyr Gln Glu Val Thr
                165                 170                 175

Pro Met Ile Asn Ser Trp Gly Val Arg Ile Arg Thr
            180                 185

<210> SEQ ID NO 8
<211> LENGTH: 274
<212> TYPE: PRT
<213> ORGANISM: Humicola lanuginosa
<220> FEATURE:
<221> NAME/KEY: VARIANT
<222> LOCATION: (1)..(274)
<220> FEATURE:
<221> NAME/KEY: mat_peptide
<222> LOCATION: (6)..(274)

<400> SEQUENCE: 8

Ser Pro Ile Arg Arg Glu Val Ser Gln Asp Leu Phe Asn Gln Phe Asn
 -5              -1   1               5                  10

Leu Phe Ala Gln Tyr Ser Ala Ala Tyr Cys Gly Lys Asn Asn Asp
             15                  20                  25

Ala Pro Ala Gly Thr Asn Ile Thr Cys Thr Gly Asn Ala Cys Pro Glu
            30                  35                  40

Val Glu Lys Ala Asp Ala Thr Phe Leu Tyr Ser Phe Glu Asp Ser Gly
        45                  50                  55

Val Gly Asp Val Thr Gly Phe Leu Ala Leu Asp Asn Thr Asn Lys Leu
60                  65                  70                  75

Ile Val Leu Ser Phe Arg Gly Ser Arg Ser Ile Glu Asn Trp Ile Gly
                80                  85                  90

Asn Leu Asn Phe Asp Leu Lys Glu Ile Asn Asp Ile Cys Ser Gly Cys
             95                 100                 105

Arg Gly His Asp Gly Phe Thr Ser Ser Trp Arg Ser Val Ala Asp Thr
            110                 115                 120

Leu Arg Gln Lys Val Glu Asp Ala Val Arg Glu His Pro Asp Tyr Arg
        125                 130                 135

Val Val Phe Thr Gly His Ser Leu Gly Gly Ala Leu Ala Thr Val Ala
140                 145                 150                 155

Gly Ala Asp Leu Arg Gly Asn Gly Tyr Asp Ile Asp Val Phe Ser Tyr
                160                 165                 170

Gly Ala Pro Arg Val Gly Asn Arg Ala Phe Ala Glu Phe Leu Thr Val
            175                 180                 185

Gln Thr Gly Gly Thr Leu Tyr Arg Ile Thr His Thr Asn Asp Ile Val
        190                 195                 200

Pro Arg Leu Pro Pro Arg Glu Phe Gly Tyr Ser His Ser Ser Pro Glu
    205                 210                 215

Tyr Trp Ile Lys Ser Gly Thr Leu Val Pro Val Arg Arg Arg Asp Ile
220                 225                 230                 235
```

```
Val Lys Ile Glu Gly Ile Asp Ala Thr Gly Gly Asn Asn Gln Pro Asn
            240                 245                 250

Ile Pro Asp Ile Pro Ala His Leu Trp Tyr Phe Gly Leu Ile Gly Thr
            255                 260                 265

Cys Leu

<210> SEQ ID NO 9
<211> LENGTH: 269
<212> TYPE: PRT
<213> ORGANISM: Humicola lanuginosa
<220> FEATURE:
<221> NAME/KEY: mat_peptide
<222> LOCATION: (1)..(269)

<400> SEQUENCE: 9

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
            115                 120                 125

Glu Asp Ala Val Arg Glu His Pro Asp Tyr Arg Val Val Phe Thr Gly
        130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 10
<211> LENGTH: 483
<212> TYPE: PRT
<213> ORGANISM: Bacillus licheniformis
<220> FEATURE:
<221> NAME/KEY: mat_peptide
<222> LOCATION: (1)..(483)

<400> SEQUENCE: 10
```

```
Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65              70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
                100                 105                 110

Glu Asp Val Thr Ala Val Glu Val Asp Pro Ala Asp Arg Asn Arg Val
            115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
                180                 185                 190

Tyr Asp Tyr Leu Met Tyr Ala Asp Ile Asp Tyr Asp His Pro Asp Val
            195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
            275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
    355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
```

-continued

```
                    420                 425                 430
Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 11
<211> LENGTH: 480
<212> TYPE: PRT
<213> ORGANISM: Bacillus amyloliquefaciens
<220> FEATURE:
<221> NAME/KEY: mat_peptide
<222> LOCATION: (1)..(480)

<400> SEQUENCE: 11

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
            20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
145                 150                 155                 160

Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
            180                 185                 190

Tyr Asp Tyr Leu Met Tyr Ala Asp Val Asp Tyr Asp His Pro Asp Val
        195                 200                 205

Val Ala Glu Thr Lys Lys Trp Gly Ile Trp Tyr Ala Asn Glu Leu Ser
    210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
            260                 265                 270

Tyr Leu Asn Lys Thr Ser Phe Asn Gln Ser Val Phe Asp Val Pro Leu
        275                 280                 285

His Phe Asn Leu Gln Ala Ala Ser Ser Gln Gly Gly Gly Tyr Asp Met
    290                 295                 300
```

```
Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
        340                 345                 350

Thr Arg Glu Ser Gly Tyr Pro Gln Val Phe Tyr Gly Asp Met Tyr Gly
    355                 360                 365

Thr Lys Gly Thr Ser Pro Lys Glu Ile Pro Ser Leu Lys Asp Asn Ile
370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
            405                 410                 415

Ser Ser Ala Ala Lys Ser Gly Leu Ala Ala Leu Ile Thr Asp Gly Pro
        420                 425                 430

Gly Gly Ser Lys Arg Met Tyr Ala Gly Leu Lys Asn Ala Gly Glu Thr
    435                 440                 445

Trp Tyr Asp Ile Thr Gly Asn Arg Ser Asp Thr Val Lys Ile Gly Ser
450                 455                 460

Asp Gly Trp Gly Glu Phe His Val Asn Asp Gly Ser Val Ser Ile Tyr
465                 470                 475                 480
```

<210> SEQ ID NO 12
<211> LENGTH: 514
<212> TYPE: PRT
<213> ORGANISM: Bacillus stearothermophilus
<220> FEATURE:
<221> NAME/KEY: mat_peptide
<222> LOCATION: (1)..(514)

<400> SEQUENCE: 12

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190
```

```
Asn Gly Asn Tyr Asp Tyr Leu Met Tyr Ala Asp Leu Asp Met Asp His
            195                 200                 205

Pro Glu Val Val Thr Glu Leu Lys Ser Trp Gly Lys Trp Tyr Val Asn
            210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
            275                 280                 285

Ala Pro Leu His Asn Lys Phe Tyr Thr Ala Ser Lys Ser Gly Gly Thr
            290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
            435                 440                 445

Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp

<210> SEQ ID NO 13
<211> LENGTH: 1620
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1620)
<223> OTHER INFORMATION: DNA encoding SEQ ID NO: 1

<400> SEQUENCE: 13
atgaaacaac aaaaacggct ttacgcccga ttgctgacgc tgttatttgc gctcatcttc      60
ttgctgcctc attctgcagc cgcggcaccg tttaacggca ccatgatgca gtattttgaa     120
```

```
tggtacttgc cggatgatgg cacgttatgg accaaagtgg ccaatgaagc caacaactta      180
tccagccttg gcatcaccgc tctttggctg ccgcccgctt acaaaggaac aagccgcagc      240
gacgtagggt acggagtata cgacttgtat gacctcggcg aattcaatca aaaagggacc      300
gtccgcacaa aatacggaac aaaagctcaa tatcttcaag ccattcaagc cgcccacgcc      360
gctggaatgc aagtgtacgc cgatgtcgtg ttcgaccata aaggcggcgc tgacggcacg      420
gaatgggtgg acgccgtcga agtcaatccg tccgaccgca accagaaaat ctcgggcacc      480
tatcaaatcc aagcatggac gaaatttgat tttcccgggc ggggcaacac ctactccagc      540
tttaagtggc gctggtacca ttttgacggc gttgattggg acgaaagccg aaaattgagc      600
cgcatttaca aattccgtgg caaggcttgg gattgggaag tagacacgga attcggaaac      660
tatgactact taatgtatgc cgaccttgat atggatcatc cgaagtcgt gaccgagctg       720 aaaaactggg ggaaatggta tgtcaacaca acgaacattg atgggttccg gcttgatgcc      780
gtcaagcata ttaagttcag tttttttcct gattggttgt cgtatgtgcg ttctcagact      840
ggcaagccgc tatttaccgt cggggaatat tggagctatg acatcaacaa gttgcacaat      900
tacattacga aaacagacgg aacgatgtct ttgtttgatg ccccgttaca caacaaattt      960
tataccgctt ccaaatcagg gggcgcattt gatatgcgca cgttaatgac caatactctc     1020
atgaaagatc aaccgacatt ggccgtcacc ttcgttgata atcatgacac cgaacccggc     1080
caagcgctgc aatcatgggt cgacccatgg ttcaaaccgt ggcttacgc ctttattcta      1140 actcggcagg aaggataccc cgtgcgtcttt tatggtgact attatggcat tccacaatat    1200
aacattcctt cgctgaaaag caaaatcgat ccgctcctca tcgcgcgcag ggattatgct     1260 tacgaacgc aacatgatta tcttgatcac tccgacatca tcgggtggac aagggaaggg     1320
ggcactgaaa aaccaggatc cggactggcc gcactgatca ccgatgggcc gggaggaagc     1380
aaatggatgt acgttggcaa acaacacgct ggaaaagtgt tctatgacct taccggcaac     1440
cggagtgaca ccgtcaccat caacagtgat ggatggggggg aattcaaagt caatggcggt     1500
tcggtttcgg tttgggttcc tagaaaaacg accgtttcta ccatcgctcg gccgatcaca     1560
acccgaccgt ggactggtga attcgtccgt tggaccgaac cacggttggt ggcatggcct     1620
```

<210> SEQ ID NO 14
<211> LENGTH: 1461
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1461)
<223> OTHER INFORMATION: DNA encoding SEQ ID NO: 2

<400> SEQUENCE: 14

```
atgcctgcag cagcagccgt aaatggcacg ctgatgcagt attttgaatg gtatacgccg       60
aacgacggcc agcattggaa acgattgcag aatgatgcgg aacatttatc ggatatcggt      120
attactgccg tctggattcc cccggcatat aagggaacga gccaagcgga tgtgggctac      180
ggtgcttacg accttatga tttaggggag tttcatcaaa aagggacggt tcggacaaag       240
tacggcacaa aaggagagct gcaatctgcg atcaaaagtc ttcattcccg cgacattaac      300
gtttacgggg atgtggtcat caaccacaaa ggcggcgctg atgcgaccga agatgtaacc      360
gcggttgaag tcgatcccgc tgaccgcaac cgcgtaattt caggagaaca cctaattaaa      420
gcctggacac attttcattt tccggggcgc ggcagcacat acagcgattt taagtggtat      480
```

-continued

```
tggtaccatt tgacggaac cgattgggac gagtcccgaa agctgaaccg catctataag    540
tttcaaggga agacttggga ttgggaagtt tccaatgaat tcggcaacta tgattatttg    600
atgtatgccg acatcgatta tgaccatcct gacgtcgtag cagaaattaa gagatggggc    660
acttggtatg ccaatgaact gcaattggac ggtttccgtc ttgatgctgt caaacacatt    720
aaatttttct tttttgcggga ttgggttaat catgtcaggg aaaaaacggg aaggaaatg    780 tttacggtag ctgagtactg gtcgaatgac ttgggcgcgc tggaaaacta tttgaacaaa    840
acaaatttta atcattcagt gtttgacgtg ccgcttcatt atcagttcca tgctgcatcg    900
acacagggag gcggctatga tatgaggaaa ttgctgaacg gtacggtcgt ttccaagcat    960
ccgttgaaat cggttacatt tgtcgataac catgatacac agccggggca atcgcttgag    1020
tcgactgtcc aaacatggtt taagccgctt gcttacgctt ttattctcac aagggaatct    1080
ggataccctc aggttttcta cggggatatg tacgggacga aaggagactc ccagcgcgaa    1140
attcctgcct tgaaacacaa aattgaaccg atcttaaaag cgagaaaaca gtatgcgtac    1200
ggagcacagc atgattattt cgaccaccat gacattgtcg gctggacaag ggaaggcgac    1260
agctcggttg caaattcagg tttggcggca ttaataacag acggacccgg tggggcaaag    1320
cgaatgtatg tcggccggca aaacgccggt gagacatggc atgacattac cggaaaccgt    1380
tcggagccgg ttgtcatcaa ttcggaaggc tggggagagt ttcacgtaaa cggcgggtcg    1440
gtttcaattt atgttcaaag a    1461
```

<210> SEQ ID NO 15
<211> LENGTH: 1449
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1449)
<223> OTHER INFORMATION: DNA encoding SEQ ID NO: 3

<400> SEQUENCE: 15

```
caccataatg gtacgaacgg cacaatgatg cagtactttg aatggtatct accaaatgac    60
ggaaaccatt ggaatagatt aaggtctgat gcaagtaacc taaaagataa agggatctca    120
gcggtttgga ttcctcctgc atggaagggt gcctctcaaa atgatgtggg gtatggtgct    180
tatgatctgt atgatttagg agaattcaat caaaaaggaa ccattcgtac aaaatatgga    240
acgcgcaatc agttacaagc tgcggttaac gccttgaaaa gtaatggaat tcaagtgtat    300
ggcgatgttg taatgaatca taaaggggga gcagacgcta ccgaaatggt taaagcagtc    360
gaagtaaacc cgaataatag aaatcaagaa gtgtccggtg aatatacaat tgaggcttgg    420
acaaagtttg actttccagg acgaggtaat actcattcaa acttcaaatg gagatggtat    480
cactttgatg gagtagattg ggatcagtca cgtaagctga acaatcgaat ttataaattc    540
cgcggtaaag ggtgggattg ggaagtcgat acagaattcg gtaactatga ttacctaatg    600
tatgcagata ttgacatgga tcacccagag gtagtgaatg agctaagaaa ttggggtgtt    660
tggtatacga atacattagg ccttgatggt tttagaatag atgcagtaaa acatataaaa    720
tacagcttta ctcgtgattg gattaatcat gttagagtgc caactggcaa aaatatgttt    780
gcggttgcgg aattttgaa aaatgattta ggtgctattg aaaactattt aaacaaaaca    840
aactggaacc attcagtctt tgatgttccg ctgcactata acctctataa tgcttccaaaa    900 agcggaggga attatgatat gaggcaaata tttaatggta cagtcgtgca aaagcatcca    960
```

-continued

| | |
|---|---|
| atgcatgctg ttacatttgt tgataatcat gattcgcaac ctgaagaagc tttagagtct | 1020 |
| tttgttgaag aatggttcaa accattagcg tatgctttga cattaacacg tgaacaaggc | 1080 |
| taccttctg tattttatgg agattattat ggcattccaa cgcatggtgt accagcgatg | 1140 |
| aaatcgaaaa ttgacccgat tctagaagcg cgtcaaaagt atgcatatgg aagacaaaat | 1200 |
| gactacttag accatcataa tatcatcggt tggacacgtg aagggaatac agcacacccc | 1260 |
| aactccggtt tagctactat catgtccgat ggggcaggag gaaataagtg gatgtttgtt | 1320 |
| gggcgtaata aagctggtca agtttggacc gatatcactg gaaataaagc cggtactgtt | 1380 |
| acgattaatg ctgatggatg gggtaatttt tctgtaaatg gaggatcagt ttctatttgg | 1440 |
| gtaaacaaa | 1449 |

<210> SEQ ID NO 16
<211> LENGTH: 1768
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA encoding SEQ ID NO: 4

<400> SEQUENCE: 16

| | |
|---|---|
| gtgaggaaac gaaaaaatat gctattaagt atgtttatag tatttattat gatgctttct | 60 |
| tttgtgccag tttcaggtgg agaggtagaa gcacatcata atgggacaaa tgggacgatg | 120 |
| atgcaatact ttgaatggca cttgcctaat gatgggaatc actggaatag attaagagat | 180 |
| gatgctagta atctaagaaa tagaggtata accgctattt ggattccgcc tgcctggaaa | 240 |
| gggacttcgc aaaatgatgt ggggtatgga gcctatgatc tttatgattt aggggaattt | 300 |
| aatcaaaagg ggacggttcg tactaagtat gggacacgta gtcaattgga gtctgccatc | 360 |
| catgctttaa agaataatgg cgttcaagtt tatgggatg tagtgatgaa ccataaagga | 420 |
| ggagctgatg ctacagaaaa cgttcttgct gtcgaggtga atccaaataa ccggaatcaa | 480 |
| gaaatatctg gggactacac aattgaggct tggactaagt tgattttcc agggagggg | 540 |
| aatacatact cagactttaa atggcgttgg tatcatttcg atggtgtaga ttgggatcaa | 600 |
| tcacgacaat tccaaaatcg tatctacaaa ttccgaggtg atggtaaggc atgggattgg | 660 |
| gaagtagatt cggaaaatgg aaattatgat tatttaatgt atgcagatgt agatatggat | 720 |
| catccggagg tagtaaatga gcttagaaga tggggagaat ggtatacaaa tacattaaat | 780 |
| cttgatggat ttaggatcga tgcggtgaag catattaaat atagctttac acgtgattgg | 840 |
| ttgacccatg taagaaacgc aacggggaaa gaaatgtttg ctgttgctga attttggaaa | 900 |
| aatgatttag gtgccttgga gaactatta aataaaacaa actggaatca ttctgtcttt | 960 |
| gatgtccccc ttcattataa tctttataac gcgtcaaata gtggaggcaa ctatgacatg | 1020 |
| gcaaaacttc ttaatggaac ggttgttcaa aagcatccaa tgcatgccgt aactttttgtg | 1080 |
| gataatcacg attctcaacc tggggaatca ttagaatcat ttgtacaaga atggtttaag | 1140 |
| ccacttgctt atgcgcttat tttaacaaga gaacaaggct atccctctgt cttctatggt | 1200 |
| gactactatg gaattccaac acatagtgtc ccagcaatga agccaagat tgatccaatc | 1260 |
| ttagaggcgc gtcaaaattt tgcatatgga acacaacatg attattttga ccatcataat | 1320 |
| ataatcggat ggacacgtga aggaaatacc acgcatccca attcaggact tgcgactatc | 1380 |
| atgtcggatg ggccaggggg agagaaatgg atgtacgtag gcaaaataa agcaggtcaa | 1440 |

```
gtttggcatg acataactgg aaataaacca ggaacagtta cgatcaatgc agatggatgg    1500
gctaattttt cagtaaatgg aggatctgtt tccatttggg tgaaacgata atggaaaaaa    1560
gaaaaggcta aatggtcttt tctttttttc taggaggtgt tgtaaatgga gtttattcaa    1620
ttactaagtg ccgagctaaa agatcagtcg tatctttttt taaaattaga agcatttgtt    1680
tccgtattag atatagaggg tcatgaaaaa tgtgttatgc aatatcaaat ggggcagcag    1740
ttctttacag tgagcggcaa tgaaattg                                       1768
```